(12) United States Patent
Kumar et al.

(10) Patent No.: US 8,575,178 B2
(45) Date of Patent: Nov. 5, 2013

(54) ISOTHIAZOLO-PYRIMIDINEDIONE DERIVATIVES AS TRPA1 MODULATORS

(75) Inventors: Sukeerthi Kumar, Navi Mumbai (IN); Abraham Thomas, Navi Mumbai (IN); Sanjay Margal, Navi Mumbai (IN); Neelima Khairatkar-Joshi, Thane (IN); Indranil Mukhopadhyay, Navi Mumbai (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 24 days.

(21) Appl. No.: 13/257,241

(22) PCT Filed: Mar. 22, 2010

(86) PCT No.: PCT/IB2010/000834
§ 371 (c)(1),
(2), (4) Date: Sep. 16, 2011

(87) PCT Pub. No.: WO2010/109328
PCT Pub. Date: Sep. 30, 2010

(65) Prior Publication Data
US 2012/0010223 A1    Jan. 12, 2012

Related U.S. Application Data

(60) Provisional application No. 61/171,355, filed on Apr. 21, 2009.

(30) Foreign Application Priority Data

Mar. 23, 2009 (IN) .......................... 665/MUM/2009

(51) Int. Cl.
*A01N 43/90* (2006.01)
*A61K 31/519* (2006.01)
*C07D 471/00* (2006.01)
*C07D 487/00* (2006.01)

(52) U.S. Cl.
USPC ....................................... 514/260.1; 544/255

(58) Field of Classification Search
None
See application file for complete search history.

(56) References Cited

U.S. PATENT DOCUMENTS

2009/0062258 A1    3/2009    Hamamura et al.

FOREIGN PATENT DOCUMENTS

| GB | 1445697 | 8/1976 |
|----|---------|--------|
| WO | 98/46606 A1 | 10/1998 |
| WO | 03/000694 A1 | 1/2003 |
| WO | 2004/014916 A1 | 2/2004 |
| WO | 2004/055054 A1 | 7/2004 |
| WO | 2005/077959 A1 | 8/2005 |
| WO | 2005/089206 A2 | 9/2005 |
| WO | 2007/073505 A2 | 6/2007 |
| WO | 2007/108750 A1 | 9/2007 |
| WO | 2008/094909 A2 | 8/2008 |
| WO | 2009/002933 A1 | 12/2008 |
| WO | 2009/158719 A2 | 12/2009 |

OTHER PUBLICATIONS

International Search Report dated Oct. 6, 2010, from corresponding International Application No. PCT/IB2010/000930.
International Search Report dated Aug. 26, 2010, from corresponding International Application No. PCT/IB2010/000553.
International Search Report dated Jun. 28, 2010, from corresponding International Application No. PCT/IB2010/000840.
Foley, Kathleen M.: "Problems of Overarching Importance Which Transcend Organ Systems", Cecil Textbook of Medicine, J. C. Bennett & F. Plum (eds.), vol. 20, 1996, pp. 100-107.
Gianella, Mario et al.: "Benzisoxazole and Benzisothiazole Analogs of Auxin", Phytochemistry, vol. 10, 1971, pp. 539-544.
Hirota, Kosaku et al.: "Stable Thioaldehydes: Synthesis, Structure Assignment, and Stability of 6-Amino-5-thioformyluracils", Tetrahedron, vol. 52, No. 30, 1996, pp. 9971-9978.
Itoh, Tsuneo et al.: "Photochemical Synthesis of Fused Tricyclic Compounds from Bis-6,6'-(1,3-dialkyluracilyl) sulfides1-3", Chem. Pharma. Bull., vol. 29, No. 4, 1981, pp. 1039-1043.
King, Carroll L. et al.: "The Reaction of Ketones with Iodine and Thiourea1", J. Am. Chem. Soc., vol. 72, 1950, pp. 3722-3725.
Kotha, Sambasivarao et al.: "A Simple Synthetic Approach to Allylated Aromatics via the Suzuki-Miyaura Cross-Coupling Reaction", Synlett, vol. 12, 2005, pp. 1877-1890.

(Continued)

*Primary Examiner* — Jeffrey Murray
(74) *Attorney, Agent, or Firm* — Pergament Gilman & Cepeda LLP; Milagros A. Cepeda; Edward D. Pergament

(57) ABSTRACT

The present invention is related to novel isothiazolo[3,4-d] pyrimidinedione and isothiazolo[5,4-d]pyrimidinedione derivatives as TRPA (Transient Receptor Potential subfamily A) modulators. In particular, compounds described herein are useful for treating or preventing diseases, conditions and/or disorders modulated by TRPA1 (Transient Receptor Potential subfamily A, member 1). Also provided herein are processes for preparing compounds described herein, intermediates used in their synthesis, pharmaceutical compositions thereof, and methods for treating or preventing diseases, conditions and/or disorders modulated by TRPA1.

15 Claims, No Drawings

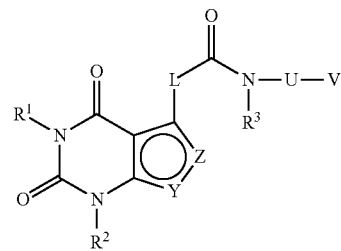

(I)

(56) References Cited

OTHER PUBLICATIONS

MacPherson, Lindsey J. et al.: "Noxious compounds activate TRPA1 ion channels through covalent modification of cysteines", Nature, vol. 445, Feb. 1, 2007, pp. 541-545.

McMahon, Stephen B. et al.: "Increasingly Irritable and Close to Tears: TRPA1 in Inflammatory pain", Cell, vol. 124, 2006, pp. 1123-1125.

McNamara, Colleen R. et al.: "TRPA1 mediates formalin-induced pain", Proc. Natl. Acad. Sci. U.S.A., vol. 104, Aug. 14, 2007, pp. 13525-13530.

Naik, Samir J. et al.: "Synthesis and application of novel 4,5,6,7-tetrahydrobenzothiazole based azo disperse dyes", Arkivoc, vol. xiiii, Apr. 21, 2005, pp. 141-149.

Okuda, Hiroto et al.: "Enamino Carbodithioates. III.1) Methyl 6-Aminouracil-5-carbodithioates. (3). Methylthiosothiazolo[3,4-d]pyrimidine-4,6(5H,7H)-diones", Pharmaceutical Society of Japan, vol. 99. No. 10, 1979, pp. 989-992.

Okuda, Hiroto et al.: "Synthesis and Reactions of 3-Methylthioisothiazolo[3,4d]Pyrimidine-4,6 (5H,7H)-DIONES1)", Heterocycles, vol. 12, No. 4, 1979, pp. 485-488.

Posner, Theodor et al.: "Kenntnis der ungesattigten Verbindungen. X. Uber die Einwirkung von frelem Hydroxylamin auf Cumarine.", Chem. Ber., vol. 46, 1913, pp. 3816-3833.

Prajapati, Dipak et al.: "Studies on Pyrimidine-Annelated Heterocycles; 8.1 Intramolecular Cycloaddition of Thiophene and Nitrile Oxide or Nitrone Groups Bonded to 1,3-Dimethyluracils", Synthesis,1988, pp. 342-344.

Story, Gina M. et al.: "ANKTM1, a TRP-like Channel Expressed in Nociceptive Neurons, Is Activated by Cold Temperatures", Cell, vol. 112, Mar. 21, 2003), pp. 819-829.

Toth, Attila et al.: "Arachidonyl dopamine as a ligand for the vanilloid receptor VR1 of the rat", Life Sciences, vol. 73, 2003, pp. 487-498.

Voorhoeve, P. Mathijs et al.: "A Genetic Screen Implicates miRNA-372 and miRNA-373 As Oncogenes in Testicular Germ Cell Tumors", Cell, vol. 124, Mar. 24, 2006, pp. 1169-1181.

Wissenbach, Ulrich et al.: "TRP channels as potential drug targets", Biology of the Cell, vol. 96, 2004, pp. 47-54.

Okuhara, Dayne Y. et al.: "Transient receptor potential channels as drug targets", Expert Opinion on Therapeutic Targets, vol. 11, No. 3, 2007, pp. 391-401.

Duffin, G. F. et al.: "The Reaction of Diazonium Salts with 1-Aryl-2-pyrazolines", J. Chem. Soc., 1954, pp. 408-415.

Prakash, G. K. Surya et al.: "N-Halosuccinimide/BF3-H2O, Efficient Electrophilic Halogenating Systems for Aromatics", J. Am. Chem. Soc. vol. 126, 2004, pp. 15770-15776.

International Search Report and Written Opinion of International Patent Application No. PCT/IB2010/001073, mailed Sep. 20, 2010.

Supplemental European Search Report of EP 10755503, dated Jun. 25, 2012.

International Search Report dated Jun. 28, 2010 from corresponding International Application No. PCT/IB2010/000834.

ISOTHIAZOLO-PYRIMIDINEDIONE DERIVATIVES AS TRPA1 MODULATORS

RELATED APPLICATIONS

This application is a National Stage Application under 35 U.S.C. 371 of PCT International Application No. PCT/IB2010/000834, filed Mar. 22, 2010, which claims priority to Indian Patent Application No 665/MUM/2009 filed on Mar. 23, 2009 and U.S. Provisional Application No. 61/171,355 filed on Apr. 21, 2009 all of which are hereby incorporated by reference.

TECHNICAL FIELD

The present patent application relates to isothiazolo[3,4-d]pyrimidinedione and isothiazolo[5,4-d]pyrimidinedione derivatives with transient receptor potential ankyrin1 (TRPA1) activity.

BACKGROUND OF THE INVENTION

The transient receptor potential (TRP) channels or receptors are pain receptors. They have been classified into seven subfamilies: TRPC (canonical), TRPV (vanilloid), TRPM (melastatin), TRPP (polycystin), TRPML (mucolipin), TRPA (ankyrin, ANKTM1) and TRPN (NOMPC) families. The TRPC family can be divided into 4 subfamilies (i) TRPC1 (ii) TRPC2 (iii) TRPC3, TRPC6, TRPC7 and (iv) TRPC4, TRPC5 based on sequence functional similarities. Currently the TRPV family has 6 members. TRPV5 and TRPV6 are more closely related to each other than to TRPV1, TRPV2, TRPV3 or TRPV4. TRPA1 is most closely related to TRPV3 and is more closely related to TRPV1 and TRPV2 than to TRPV5 and TRPV6. The TRPM family has 8 members. Constituents include the following: the founding member TRPM1 (melastatin or LTRPC1), TRPM3 (KIAA1616 or LTRPC3), TRPM7 (TRP-PLIK, ChaK(1), LTRPC7), TRPM6 (ChaK2), TRPM2 (TRPC7 or LTRPC2), TRPM8 (TRP-p8 or CMR1), TRPM5 (MTR1 or LTRPC5) and TRPM4 (F1120041 or LTRPC4). The TRPML family consists of the mucolipins, which include TRPML1 (mucolipin 1), TRPML2 (mucolipin 2) and TRPML3 (mucolipin 3). The TRPP family consists of two groups of channels: those predicted to have six transmembrane domains and those that have eleven. TRPP2 (PKD2), TRPP3 (PKD2L1), TRPP5 (PKD2L2) are all predicted to have six transmembrane domains. TRPP1 (PKD1, PC1), PKD-REJ and PKD-1L1 are all thought to have eleven transmembrane domains. The sole mammalian member of the TRPA family is ANKTM1.

It is believed TRPA1 is expressed in nociceptive neurons. Nociceptive neurons of the nervous system sense the peripheral damage and transmit pain signals. TRPA1 is membrane bound and most likely acts as a heterodimeric voltage gated channel. It is believed to have a particular secondary structure, its N-terminus is lined with a large number of ankyrin repeats which are believed to form a spring-like edifice. TRPA1 is activated by a variety of noxious stimuli, including cold temperatures (activated at 17° C.), pungent natural compounds (e.g., mustard, cinnamon and garlic) and environmental irritants (MacPherson L J et al, *Nature*, 2007, 445; 541-545). Noxious compounds activate TRPA1 ion channels through covalent modification of cysteines to form covalently linked adducts. Variety of endogenous molecules produced during tissue inflammation/injury have been identified as pathological activators of TRPA1 receptor. These include hydrogen peroxide which is produced due to oxidative stress generated during inflammation, alkenyl aldehyde 4-HNE—an intracellular lipid peroxidation product and cyclopentenone prostaglandin 15dPGJ2 which is produced from PGD2 during inflammation/allergic response. TRPA1 is also activated in receptor dependant fashion by Bradykinin (BK) which is released during tissue injury at peripheral terminals The difference between TRPA1 and other TRP receptors is that TRPA1 ligand binding persists for hours due to which the physiological response (e.g., pain) is greatly prolonged. Hence to dissociate the electrophile, an effective antagonist is required.

WO 2009/158719, WO 2009/002933, WO 2008/0949099, WO 2007/073505, WO 2004/055054 and WO 2005/089206 describe the TRP channels as the targets for the treatment of pain and related conditions.

In efforts to discover better analgesics for the treatment of both acute and chronic pain and to develop treatments for various neuropathic and nociceptive pain states, there exists a need for a more effective and safe therapeutic treatment of diseases, conditions and/or disorders modulated by TRPA1.

SUMMARY OF THE INVENTION

The present invention relates to compounds of the formula (I):

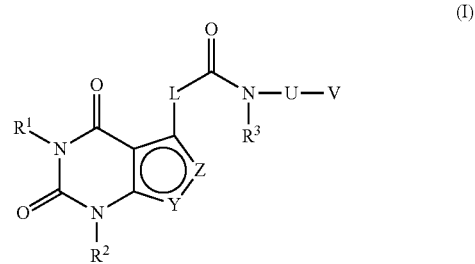

or a pharmaceutically acceptable salt thereof,
wherein,

Y and Z are independently selected from sulfur or nitrogen; with the proviso that Y and Z are not same simultaneously;

$R^1$ and $R^2$, which may be same or different, are independently selected from hydrogen, hydroxyl, substituted or unsubstituted alkyl, haloalkyl, alkenyl, alkynyl, cycloalkyl, cycloalkylalkyl, arylalkyl, $(CR^xR^y)_nOR^x$, $COR^x$, $COOR^x$, $CONR^xR^y$, $(CH_2)_nNR^xR^y$, $(CH_2)_nCHR^xR^y$ and $(CH_2)_nNHCOR^x$;

$R^3$ is selected from hydrogen, substituted or unsubstituted alkyl, alkenyl, haloalkyl, alkynyl, cycloalkyl, cycloalkylalkyl, cycloalkenyl;

L is a linker selected from —$(CR^xR^y)_n$—, —O—$(CR^xR^y)_n$—, —C(O)—, —$NR^x$—, —$S(O)_mNR^x$—, —$NR^x(CR^xR^y)_n$— and —$S(O)_mNR^x(CR^xR^y)_n$;

U is selected from substituted or unsubstituted aryl, substituted or unsubstituted five membered heterocycles such as thiazole, isothiazole, oxazole, isoxazole, thiadiazole, oxadiazole, pyrazole, imidazole, furan, thiophene, pyrroles, 1,2,3-triazoles or 1,2,4-triazole; and substituted or unsubstituted six membered heterocycles such as pyrimidine, pyridine or pyridazine;

V is selected from hydrogen, cyano, nitro, —$NR^xR^y$, halogen, hydroxyl, substituted or unsubstituted alkyl, alkenyl, alkynyl, cycloalkyl, cycloalkylalkyl, cycloalkenyl, haloalkyl, haloalkoxy, cycloalkylalkoxy, aryl, arylalkyl, biaryl, heteroaryl, heteroarylalkyl, heterocyclic ring and heterocyclylalkyl, —C(O)OR$^x$, —OR$^x$, —C(O)NR$^x$R$^y$, —C(O)R$^x$ and —SO$_2$NR$^x$R$^y$; or U and V may joined together to form an optionally substituted 3 to 7 membered saturated or unsaturated cyclic ring, which may optionally include one or more heteroatoms selected from O, S and N;

at each occurrence R$^x$ and R$^y$ are independently selected from hydrogen, hydroxyl, halogen, substituted or unsubstituted alkyl, alkenyl, alkynyl, cycloalkyl, cycloalkylalkyl, cycloalkenyl, aryl, arylalkyl, heteroaryl, heteroarylalkyl, heterocyclic ring and heterocyclylalkyl; and at each occurrence 'm' and 'n' are independently selected from 0 to 2, both inclusive.

The embodiments below are illustrative of the present invention and are not intended to limit the claims to the specific embodiments exemplified.

According to one embodiment, there is provided a compound of the formula (Ia):

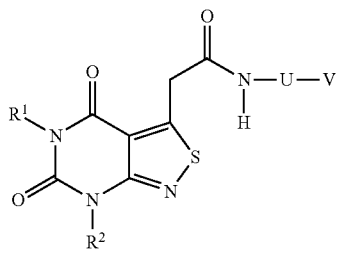

(Ia)

or a pharmaceutically acceptable salt thereof,
wherein, R$^1$, R$^2$, U and V are as defined herein above.

According to another embodiment, specifically provided are compounds of the formula (Ia) in which R$^1$ and R$^2$ are independently hydrogen or alkyl for example methyl.

According to yet another embodiment, specifically provided are compounds of the formula (Ia) in which U is substituted or unsubstituted heterocycle, preferably thiazole, pyrazole, thiadiazole or isoxazole and the substituent is alkyl, halogen, haloalkyl, haloalkoxy or aryl.

According to yet another embodiment, specifically provided are compounds of the formula (Ia) in which V is substituted or unsubstituted aryl, preferably phenyl. In this embodiment the substituents on phenyl may be one or more are independently selected from alkyl (for example ethyl, tert-butyl), halogen (for example F, Cl or Br), haloalkyl (for example CF$_3$), haloalkoxy (for example OCF$_3$ or OCHF$_2$) and cycloalkyl (for example cyclohexyl).

According to yet another embodiment, there is provided a compound of the formula (Ib):

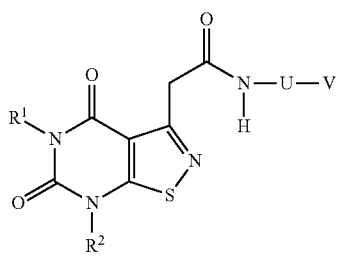

(Ib)

or a pharmaceutically acceptable salt thereof,
wherein, R$^1$, R$^2$, U and V are as defined herein above.

According to yet another embodiment, specifically provided are compounds of the formula (Ib) in which R$^1$ and R$^2$ are independently hydrogen or alkyl for example methyl.

According to yet another embodiment, specifically provided are compounds of the formula (Ib) in which U is substituted or unsubstituted heterocycle, preferably thiazole, pyrazole, thiadiazole or isoxazole and the substituent is halogen, haloalkyl haloalkoxy or aryl.

According to yet another embodiment, specifically provided are compounds of the formula (Ib) in which V is substituted or unsubstituted aryl, preferably phenyl. In this embodiment the substituents on phenyl may be one or more are independently selected from alkyl (for example ethyl, tert-butyl), halogen (for example F, Cl or Br), haloalkyl (for example CF$_3$), haloalkoxy (for example OCF$_3$ or OCHF$_2$) and cycloalkyl (for example cyclohexyl).

According to yet another embodiment, there is provided a compound of the formula (Ic):

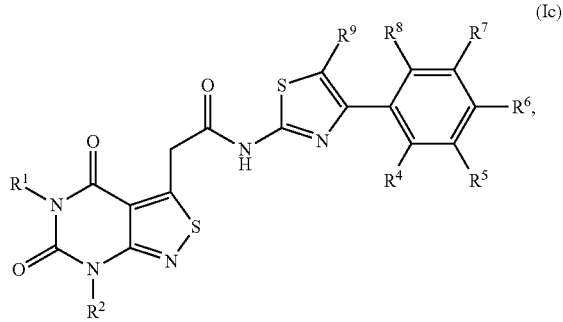

(Ic)

or a pharmaceutically-acceptable salt thereof.
wherein, R$^1$ and R$^2$, which may be the same or different, are each independently hydrogen or (C$_1$-C$_4$)alkyl; and R$^4$, R$^5$, R$^6$, R$^7$, R$^8$ and R$^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

According to yet another embodiment, specifically provided are compounds of the formula (Ic) in which R$^1$ and R$^2$ are independently hydrogen or alkyl for example methyl.

According to yet another embodiment, specifically provided are compounds of the formula (Ic) in R$^4$, R$^5$, R$^6$ and R$^7$ are independently selected from alkyl (for example ethyl, tert-butyl), halogen (for example F, Cl or Br), haloalkyl (for example CF$_3$), haloalkoxy (for example OCF$_3$ or OCHF$_2$) and cycloalkyl (for example cyclohexyl).

According yet another embodiment, specifically provided are compounds of the formula (Ic) in which R$^8$ is hydrogen.

According yet another embodiment, specifically provided are compounds of the formula (Ic) in which R$^9$ is hydrogen.

According to yet another embodiment, there is provided a compound of the formula (Id):

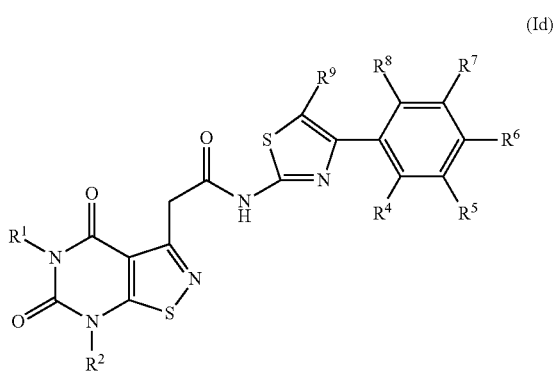

(Id)

or a pharmaceutically-acceptable salt thereof.

wherein, $R^1$ and $R^2$, which may be the same or different, are each independently hydrogen or $(C_1-C_4)$alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

According to yet another embodiment, specifically provided are compounds of the formula (Id) in $R^4$, $R^5$, $R^6$ and $R^7$ are independently selected from alkyl (for example ethyl, tert-butyl), halogen (for example F, Cl or Br), haloalkyl (for example $CF_3$), haloalkoxy (for example $OCF_3$ or $OCHF_2$) and cycloalkyl (for example cyclohexyl).

According yet another embodiment, specifically provided are compounds of the formula (Id) in which $R^8$ is hydrogen.

According yet another embodiment, specifically provided are compounds of the formula (Id) in which $R^9$ is hydrogen.

Particularly contemplated are compounds of the formulas (I), (Ia), (Ib), (Ic) and (Id) which possess $IC_{50}$ of less than 250 nM, preferably, less than 100 nM, more preferably, less than 50 nM with respect to TRPA1 activity as measured by method as described in the present patent application.

It should be understood that the compounds of the formulas (I), (Ia), (Ib), (Ic) and (Id) structurally encompasses all stereoisomers, enantiomers and diastereomers and pharmaceutically acceptable salts that may be contemplated from the chemical structure of the genera described herein.

The compound of the present invention as TRPA1 modulator is used herein because it is more selective for one TRP isoform than others, e.g., 2-fold, 5-fold, 10-fold, and more preferably at least 20, 40, 50, 60, 70, 80, or at least 100- or even 1000-fold more selective for TRPA1 over one or more of TRPC6, TRPV5, TRPV6, TRPM8, TRPV1, TRPV2, TRPV4, and/or TRPV3.

In accordance with another aspect, the present patent application provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present patent application may be associated with a pharmaceutically acceptable excipient (such as a carrier or a diluent) or be diluted by a carrier, or enclosed within a carrier which can be in the form of a capsule, sachet, paper or other container.

The compounds of the present invention can be administered as pharmaceutical composition containing, for example, 0.1 to 99.5% (more preferably, 0.5 to 90%) of active ingredient in combination with a pharmaceutically acceptable carrier. The ultimate dose will depend on the condition being treated, the route of administration and the age, weight and condition of the patient and will be the doctor's discretion.

Compounds of the present invention may be used in the manufacture of medicaments for the treatment of any diseases disclosed herein. The compounds and pharmaceutical compositions described herein are useful for modulating TRPA1 receptors, wherein modulation is believed to be related to a variety of disease states.

The compound of the present invention can be administered alone or in combination with other therapeutic agents. For instance, the TRPA1 modulator is administered conjointly with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor In accordance with another aspect, the present patent application further provides a method of inhibiting TRPA1 receptors in a subject in need thereof by administering to the subject one or more compounds described herein in the amount effective to cause inhibition of such receptor.

DETAILED DESCRIPTION OF THE INVENTION

Definitions

The terms "halogen" or "halo" includes fluorine, chlorine, bromine or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl and 1,1-dimethylethyl (tert-butyl). The term "$C_{1-6}$ alkyl" refers to an alkyl chain having 1 to 6 carbon atoms. Unless set forth or recited to the contrary, all alkyl groups described herein may be straight chain or branched, substituted or unsubstituted The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl(allyl), iso-propenyl, 2-methyl-1-propenyl, 1-butenyl and 2-butenyl. Unless set forth or recited to the contrary, all alkenyl groups described herein may be straight chain or branched, substituted or unsubstituted.

The term "alkynyl" refers to a straight or branched chain hydrocarbyl radical having at least one carbon-carbon triple bond and having 2 to about 12 carbon atoms (with radicals having 2 to about 10 carbon atoms being preferred) e.g., ethynyl, propynyl and butynyl. Unless set forth or recited to the contrary, all alkynyl groups described herein may be straight chain or branched, substituted or unsubstituted.

The term "alkoxy" refers to a straight or branched, saturated aliphatic hydrocarbon radical bonded to an oxygen atom that is attached to a core structure. Examples of alkoxy groups include but are not limited to methoxy, ethoxy, propoxy, isopropoxy, butoxy, isobutoxy, tert-butoxy, pentoxy, 3-methyl butoxy and the like. Unless set forth or recited to the contrary, all alkoxy groups described herein may be straight chain or branched, substituted or unsubstituted.

The term "haloalkyl" and "haloalkoxy" means alkyl or alkoxy, as the case may be, substituted with one or more halogen atoms, where alkyl and alkoxy groups are as defined above. The term "halo" is used herein interchangeably with the term "halogen" means F, Cl, Br or I. Examples of "haloalkyl" include but are not limited to trifluoromethyl, difluoromethyl, 2,2,2-trifluoroethyl, pentafluoroethyl, pentachloroethyl 4,4,4-trifluorobutyl, 4,4-difluorocyclohexyl, chloromethyl, dichloromethyl, trichloromethyl, 1-bromoethyl and the like. Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy, 1-bromoethoxy and the like. Unless set forth or recited to the contrary, all "haloalkyl" and "haloalkoxy" groups described herein may be straight chain or branched, substituted or unsubstituted.

The term "cycloalkyl" denotes a non-aromatic mono or multicyclic ring system of 3 to about 12 carbon atoms, such as cyclopropyl, cyclobutyl, cyclopentyl and cyclohexyl. Examples of multicyclic cycloalkyl groups include, but are not limited to, perhydronapthyl, adamantyl and norbornyl groups, bridged cyclic groups or sprirobicyclic groups, e.g., spiro(4,4) non-2-yl. Unless set forth or recited to the contrary, all cycloalkyl groups described herein may be substituted or unsubstituted.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl and cyclopentylethyl. Unless set forth or recited to the contrary, all cycloalkylalkyl groups described herein may be substituted or unsubstituted.

The term "cycloalkylalkoxy" is used to denote alkoxy substituted with cycloalkyl, wherein 'alkoxy' and 'cycloalkyl' are as defined above (either in the broadest aspect or a preferred aspect). Examples of cycloalkylalkoxy groups include cyclopropylmethoxy, 1- or 2-cyclopropylethoxy, 1-, 2- or 3-cyclopropylpropoxy, 1-, 2-, 3- or 4-cyclopropyl-butoxy, cyclobutylmethoxy, 1- or 2-cyclobutylethoxy, 1-, 2- or 3-cyclobutylpropoxy, 1-, 2-, 3- or 4-cyclobutylbutoxy, cyclopentylmethoxy, 1- or 2-cyclopentylethoxy, 1-, 2- or 3-cyclopentylpropoxy, 1-, 2-, 3- or 4-cyclopentylbutoxy, cyclohexylmethoxy, 1- or 2-cyclohexylethoxy and 1-, 2- or 3-cyclohexylpropoxy. Preferably, 'cycloalkylalkoxy' is $(C_{3-6})$cycloalkyl-$(C_{1-6})$alkoxy. Unless set forth or recited to the contrary, all cycloalkylalkoxy groups described herein may be substituted or unsubstituted.

The term "cycloalkenyl" refers to a cyclic ring-containing radical having 3 to about 8 carbon atoms with at least one carbon-carbon double bond, such as cyclopropenyl, cyclobutenyl and cyclopentenyl. Unless set forth or recited to the contrary, all cycloalkenyl groups described herein may be substituted or unsubstituted.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (ie, attached or formed) by having two adjacent atoms in common (i.e., shared) with the first ring. The term "fused" is equivalent to the term "condensed". The term "aryl" embraces aromatic radicals such as phenyl, naphthyl, tetrahydronaphthyl, indane and biphenyl. Unless set forth or recited to the contrary, all aryl groups described herein may be substituted or unsubstituted.

The term "arylalkyl" refers to an aryl group as defined above directly bonded to an alkyl group as defined above, e.g., —CH$_2$C$_6$H$_5$ or —C$_2$H$_4$C$_6$H$_5$. Unless set forth or recited to the contrary, all arylalkyl groups described herein may be substituted or unsubstituted.

The term "heterocyclic ring" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoqinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl and isochromanyl. The heterocyclic ring radical may be attached to the main structure at any heteroatom or carbon atom that results in the creation of a stable structure. Unless set forth or recited to the contrary, all heterocyclic ring described herein may be substituted or unsubstituted.

The term "heterocyclyl" refers to a heterocyclic ring radical as defined above. The heterocyclyl ring radical may be attached to the main structure at any heteroatom or carbon atom that results in the creation of a stable structure. Unless set forth or recited to the contrary, all heterocyclyl groups described herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described herein may be substituted or unsubstituted.

The term "heteroaryl" refers to an aromatic heterocyclic ring radical. The heteroaryl ring radical may be attached to the main structure at any heteroatom or carbon atom that results in the creation of a stable structure. Unless set forth or recited to the contrary, all heteroaryl groups described herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described herein may be substituted or unsubstituted.

Unless otherwise specified, the term "substituted" as used herein refers to substitution with any one or more or any combination of the following substituents: hydroxy, halogen, carboxyl, cyano, nitro, oxo (=O), thio (=S), substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstiuted guanidine, $-COOR^{x'}$, $-C(O)R^{x'}$, $-C(S)R^{x'}$, $-C(O)NR^{x'}R^{y'}$, $-C(O)ONR^{x'}R^{y'}$, $-NR^{x'}CONR^{y'}R^{z'}$, $-N(R^{x'})SOR^{y'}$, $-N(R^{x'})SO_2R^{y'}$, $-(=N-N(R^{x'})R^{y'})$, $-NR^{x'}C(O)OR^{y'}$, $-NR^{x'}R^{y'}$, $-NR^{x'}C(O)R^{y'}$, $-NR^{x'}C(S)R^{y'}$, $-NR^{x'}C(S)NR^{y'}R^{z'}$, $-SONR^{x'}R^{y'}$, $-SO_2NR^{x'}R^{y'}$, $-OR^{x'}$, $-OR^{x'}C(O)NR^{y'}R^{z'}$, $-OR^{x'}C(O)OR^{y'}$, $-OC(O)R^{x'}$, $-OC(O)NR^{x'}R^{y'}$, $-R^{x'}NR^{y'}C(O)R^{z'}$, $-R^{x'}OR^{y'}$, $-R^{x'}C(O)OR^{y'}$, $-R^{x'}C(O)NR^{y'}R^{z'}$, $-R^{x'}C(O)R^{y'}$, $-R^{x'}OC(O)R^{y'}$, $-SR^{x'}$, $-SOR^{x'}$, $-SO_2R^{x'}$ and $-ONO_2$, wherein $R^{x'}$, $R^{y'}$ and $R^{z'}$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl or substituted or unsubstituted heterocyclic ring.

The term "treating" or "treatment" of a state, disorder or condition includes; (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compounds described in the present patent application may form salts. Non-limiting examples of pharmaceutically acceptable salts forming part of this patent application include salts derived from inorganic bases salts of organic bases, salts of chiral bases, salts of natural amino acids and salts of non-natural amino acids.

Certain compounds of the present invention, including compounds of formula (I), (Ia), (Ib), (Ic) and (Id) are capable of existing in stereoisomeric forms (e.g. diastereomers and enantiomers). The present invention includes these stereoisomeric forms (including diastereomers and enantiomers) and mixtures of them. The various stereoisomeric forms of the compounds of the present invention may be separated from one another by methods known in the art or a given isomer may be obtained by stereospecific or asymmetric synthesis. Tautomeric forms and mixtures of compounds described herein are also contemplated.

Pharmaceutical Compositions

The pharmaceutical composition of the present patent application includes at least one compound described herein and at least one pharmaceutically acceptable excipient (such as a pharmaceutically acceptable carrier or diluent). Preferably, the pharmaceutical composition includes the compound(s) described herein in an amount sufficient to inhibit TRPA1 in a subject (e.g., a human). The inhibitory activity of compounds falling within the formulas (I), (Ia), (Ib), (Ic) and (Id) may be measured by an assay provided below.

The compound of the present invention may be associated with a pharmaceutically acceptable excipient (such as a carrier or a diluent) or be diluted by a carrier, or enclosed within a carrier which can be in the form of a capsule, sachet, paper or other container.

The pharmaceutical compositions may be prepared by techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

Methods of Treatment

The compounds and pharmaceutical compositions of the present invention can be administered to treat any disorder, condition, or disease treatable by inhibition of TRPA1. For instance, the compounds and pharmaceutical compositions of the present invention are suitable for treatment or prophylaxis of the following diseases, conditions and disorders mediated or associated with the activity of TRPA1 receptors: pain, chronic pain, complex regional pain syndrome, neuropathic pain, postoperative pain, rheumatoid arthritic pain, osteoarthritic pain, back pain, visceral pain, cancer pain, algesia, neuralgia, migraine, neuropathies, chemotherapy-induced neuropathies, eye-irritation, bronchial-irritation, skin-irritation (atopic dermatitis), Frost-bites (cold-bite), spasticity, catatonia, catalepsy, parkinsons, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus. The connection between therapeutic effect and inhibition of TRPA1 is illustrated, for example, in Story, G. M. et al. *Cell,* 2003, 112, 819-829; McMahon, S. B. and Wood, J. N., *Cell,* 2006, 124, 1123-1125; Voorhoeve, P. M. et al. *Cell,* 2006, 124, 1169-1181; Wissenbach, U, Niemeyer, B. A. and Flockerzi, V. *Biology of the Cell,* 2004, 96, 47-54; and the references cited therein.

Pain can be acute or chronic. While acute pain is usually self-limiting, chronic pain persists for 3 months or longer and can lead to significant changes in a patient's personality; lifestyle, functional ability and overall quality of life (K. M. Foley, *Pain,* in Cecil Textbook of Medicine; J. C. Bennett & F. Plum (eds.), 20th ed., 1996, 100-107). The sensation of pain can be triggered by any number of physical or chemical stimuli and the sensory neurons which mediate the response to this harmful stimulus are termed as "nociceptors". Nociceptors are primary sensory afferent (C and Aδ fibers) neurons that are activated by a wide variety of noxious stimuli including chemical, mechanical, thermal and proton (pH<6) modalities. Nociceptors are the nerves which sense and respond to parts of the body which suffer from damage. They signal tissue irritation, impending injury, or actual injury. When activated, they transmit pain signals (via the peripheral nerves as well as the spinal cord) to the brain.

Chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. The pain is typically well localized, constant and often with an aching or throbbing quality. Visceral pain is the subtype of nociceptive pain that involves the internal organs. It tends to be episodic and poorly localized. Nociceptive pain is usually time limited, meaning when the tissue damage heals, the pain typically resolves (arthritis is a notable exception in that it is not time limited).

General Methods of Preparation

The compounds described herein, including compounds of general formula (I), (Ia), (Ib) and (Ic) and specific examples, can be prepared by techniques known to one in the art, for example, through the reaction scheme depicted in Schemes 1-10. Furthermore, in the following scheme, where specific acids, bases, reagents, coupling agents, solvents etc. are mentioned, it is understood that other suitable acids, bases, reagents, coupling agents etc. may be used and are included within the scope of the present invention. Modifications to reaction conditions, for example, temperature, duration of the reaction or combinations thereof are envisioned as part of the present invention. The compounds obtained by using the general reaction scheme may be of insufficient purity. These compounds can be purified by any of the methods for purification of organic compounds known in the art, for example, crystallization or silica gel or alumina column chromatography using different solvents in suitable ratios. All possible stereo isomers are envisioned within the scope of this invention.

A general approach for the synthesis of isothiazolo pyrimidinyl acetamides of the general formula (I), wherein Y, Z, $R^1$, $R^2$, $R^3$, U, V and L are as defined above in the general description can be prepared as described in Scheme 1. Coupling reaction of a carboxylic acid of the formula (1) with amines of the general formula (2) in the presence of a suitable coupling agent such as 1-ethyl-3-(3'-dimethylaminopropyl) carbodiimide hydrochloride (EDCI) using a suitable base and solvent gives compounds of the formula (3). The selective N-alkylation of the compounds of the formula (3) with suitable alkylating agent of the formula (4) in the presence of base and solvent gives compounds of the general formula (I).

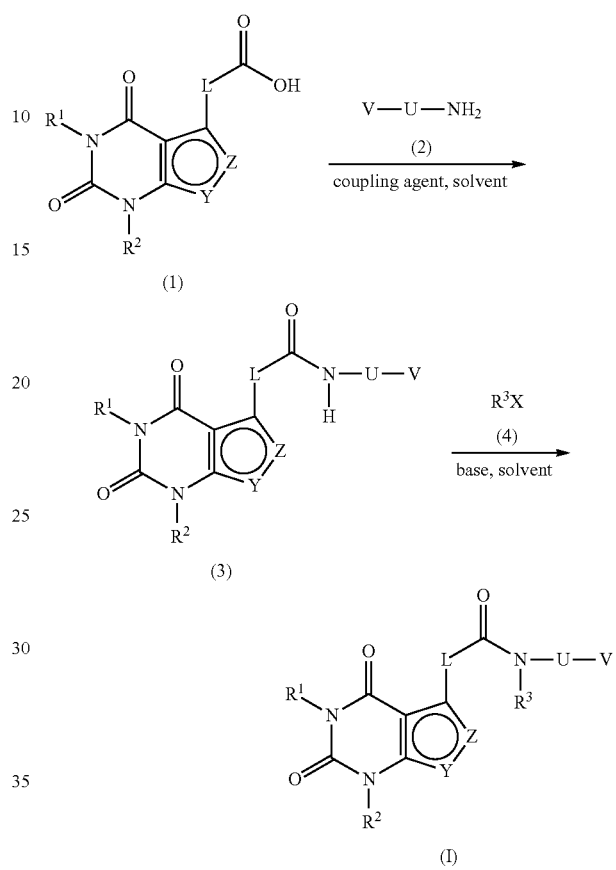

An approach for the synthesis of isothiazolo[3,4-d]pyrimidinyl acetamides of the formula (Ia), wherein $R^1$, $R^2$, U and V are as defined above is prepared as depicted in Scheme 2. 6-Amino-1,3-dialkyl uracil-5-carbodithioate (6) is obtained by the reaction of 6-amino-1,3-dialkyl uracil (5) with carbon disulphide and dimethyl sulfate in the presence of suitable base as reported by Kobayashi G. et al. *Yakugaku Zasshi,* 1979, 515-520. Oxidative cyclisation of compounds of the formula (6) using iodine in the presence of suitable solvent gives 3-methylsulfanylisothiazolo[3,4-d]pyrimidinedione (7) according to the procedure described by Kobayashi G. et al. *Yakugaku Zasshi,* 1979, 989-992 and Kobayashi, G. et. al. *Heterocycles,* 1979, 485-488. The oxidation of methylsulfanyl isothiazole (7) using oxone in the presence of a suitable solvent furnished the expected sulphone derivative (8) in good yield. Reaction of sulphone (8) with dialkyl malonoate (9) in the presence of suitable base such as sodium hydride in a suitable solvent gives the diester of the formula (10) (wherein R is alkyl). Dealkoxycarbonylation of diester (10) using suitable base such as sodium hydride afforded desired isothiazolo[3,4-d]pyrimidinyl ester (11). Hydrolysis of the ester (11) with aqueous acid gives compounds of the formula (12). The carboxylic acid of formula (12) is coupled with an amine of the general formula (2) in the presence of a suitable coupling agent such as EDCI to give compounds represented by the general formula (Ia).

Scheme 2

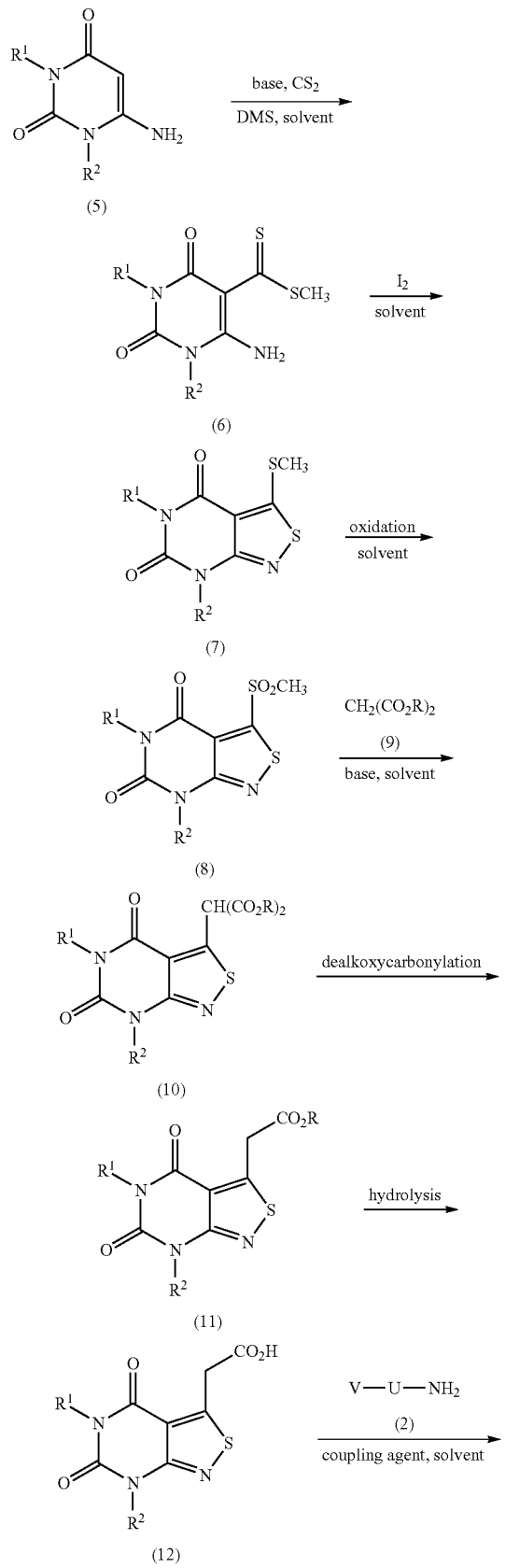

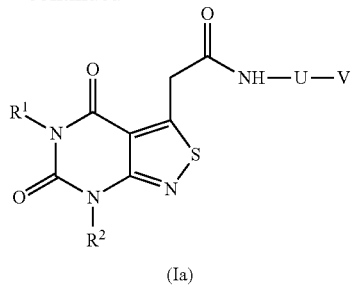

Another approach for the synthesis of isothiazolo[3,4-d]pyrimidinyl acetamides of the formula (Ia) is as shown in Scheme 3. Displacement of methylsulfonyl group of intermediate (8) with an active ester of the formula (13) (wherein R is alkyl) in the presence of a suitable base gives compounds of the formula (14). Dealkoxycarbonylation of (14) in the presence of suitable base and solvent gives the compounds of the general formula (Ia).

Scheme 3

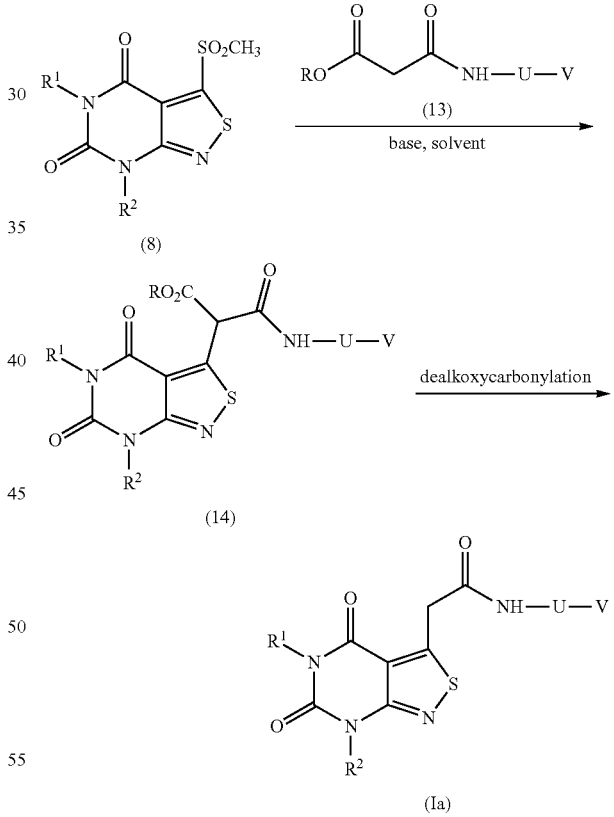

An alternative approach for the synthesis isothiazolo[3,4-d]pyrimidinyl acetamides of the formula (Ia) is as described in Scheme 4. Compounds of the formula (15) can be prepared from commercially available 6-aminouracil of the formula (5) in two steps according to reported procedure (Hirota, K. et al. *Tetrahedron*, 1996, 52, 9971-9978). Cyclisation of compounds of the formula (15) using lead tetraacetate in suitable solvent gives fused isothiazole derivative of the formula (16), which on halogenation using N-bromosuccinimide or N-iodosuccinimide in $BF_3$-etherate or trifluoromethanesulphonic acid gives compounds of the formula (17). This conversion is according to procedure reported by George, O. L. et al. *J. Am. Chem.*, 2004, 126, 15770-15776. The halide (17) can be transformed to the corresponding allyl isothiazole derivative of the formula (19) by a Suzuki-Miyaura coupling reaction with allyl boronic acids of formula (18) in the presence of Pd (O) using a procedure similar to the Suzuki-Miyaura coupling reaction described by Kotha et al. *Synlett* 2005, 12, 1877-1890. Compound of the formula (19) is transformed to the carboxylic acid (12) using oxidative cleavage of the terminal olefin by methods well known in the literature. The coupling of compounds of formula (12) with an amine of the general formula (2) by using a standard amide coupling method gives compounds of general formula (Ia).

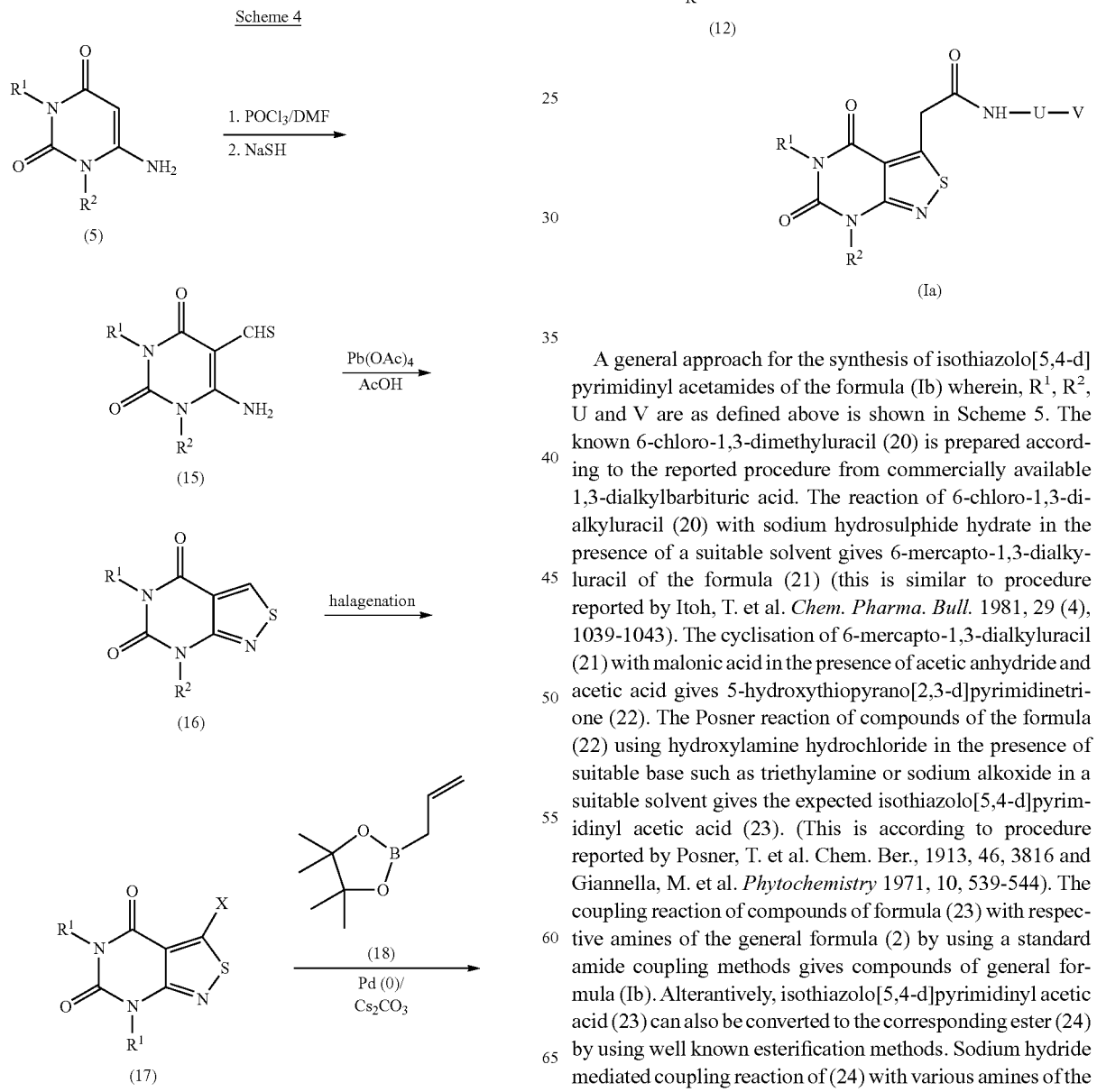

A general approach for the synthesis of isothiazolo[5,4-d]pyrimidinyl acetamides of the formula (Ib) wherein, $R^1$, $R^2$, U and V are as defined above is shown in Scheme 5. The known 6-chloro-1,3-dimethyluracil (20) is prepared according to the reported procedure from commercially available 1,3-dialkylbarbituric acid. The reaction of 6-chloro-1,3-dialkyluracil (20) with sodium hydrosulphide hydrate in the presence of a suitable solvent gives 6-mercapto-1,3-dialkyluracil of the formula (21) (this is similar to procedure reported by Itoh, T. et al. *Chem. Pharma. Bull.* 1981, 29 (4), 1039-1043). The cyclisation of 6-mercapto-1,3-dialkyluracil (21) with malonic acid in the presence of acetic anhydride and acetic acid gives 5-hydroxythiopyrano[2,3-d]pyrimidinetrione (22). The Posner reaction of compounds of the formula (22) using hydroxylamine hydrochloride in the presence of suitable base such as triethylamine or sodium alkoxide in a suitable solvent gives the expected isothiazolo[5,4-d]pyrimidinyl acetic acid (23). (This is according to procedure reported by Posner, T. et al. Chem. Ber., 1913, 46, 3816 and Giannella, M. et al. *Phytochemistry* 1971, 10, 539-544). The coupling reaction of compounds of formula (23) with respective amines of the general formula (2) by using a standard amide coupling methods gives compounds of general formula (Ib). Alterantively, isothiazolo[5,4-d]pyrimidinyl acetic acid (23) can also be converted to the corresponding ester (24) by using well known esterification methods. Sodium hydride mediated coupling reaction of (24) with various amines of the general formula (2) gives amides of the general formula (Ib).

Scheme 5

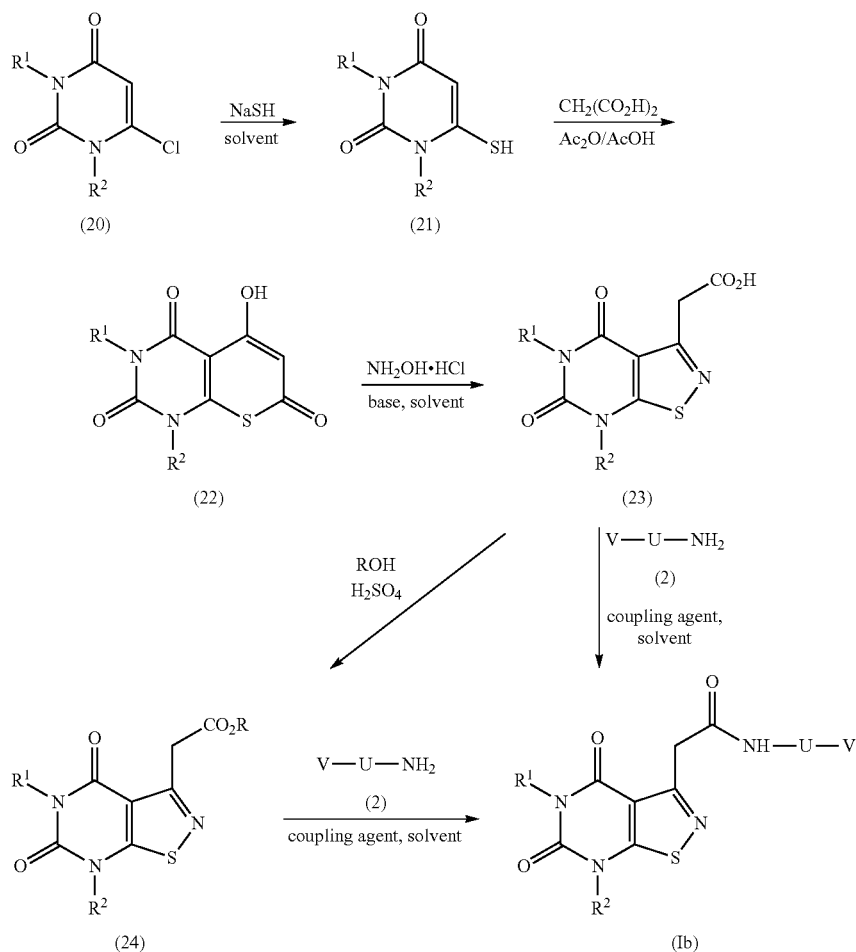

Another approach for the synthesis of isothiazolo[5,4-d]pyrimidinyl acetamides of the formula (Ib) is as shown in Scheme 6. Synthesis starts from readily available barbituric acid of the formula (25). The known 6-chloro-5-formyluracil of the formula (26) is prepared according to the reported procedure (Singh, J. S. et al, *Synthesis* 1988, 342-344). The reaction of 6-chloro-5-formyl-1,3-dialkyluracil (26) with hydroxylamine in methanol followed by dehydration with phosphorous oxychloride gives 6-chloro-5-cyano-1,3-dialkyluracil of the formula (27). 6-Chloro-5-cyano-1,3-dialkyluracil of the formula (27) can be converted to 6-mercapto-5-cyanouracil derivative (28) by its reaction with sodium hydrosulphide hydrate. The cyclisation of 6-mercapto-5-cyano deriavative (28) using chloramines in the presence of suitable solvent gives aminoisothiazole (29). The aminoisothiazole (29) on diazotization followed by halide substitution with copper halide (such as copper bromide or copper iodide) gives a halide derivative of the formula (30). The halide (30) can be transformed into allyl isothiazole of the formula (31) by Suzuki-Miyaura coupling reaction with allyl boronic acid pinacol ester of the formula (18) as described in Scheme 4. Allyl isothiazole of the formula (31) can be converted to isothiazolo[5,4-d]pyrimidinylacetic acid of the formula (23) by oxidative cleavage of the terminal double bond using an appropriate oxidizing agent in a suitable solvent. The coupling of compounds of formula (23) with an amine of the general formula (2) by using a standard amide coupling method gives compounds of general formula (Ib).

Scheme 6

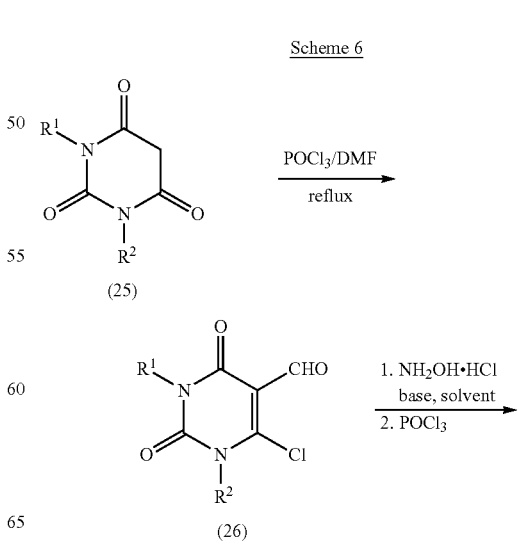

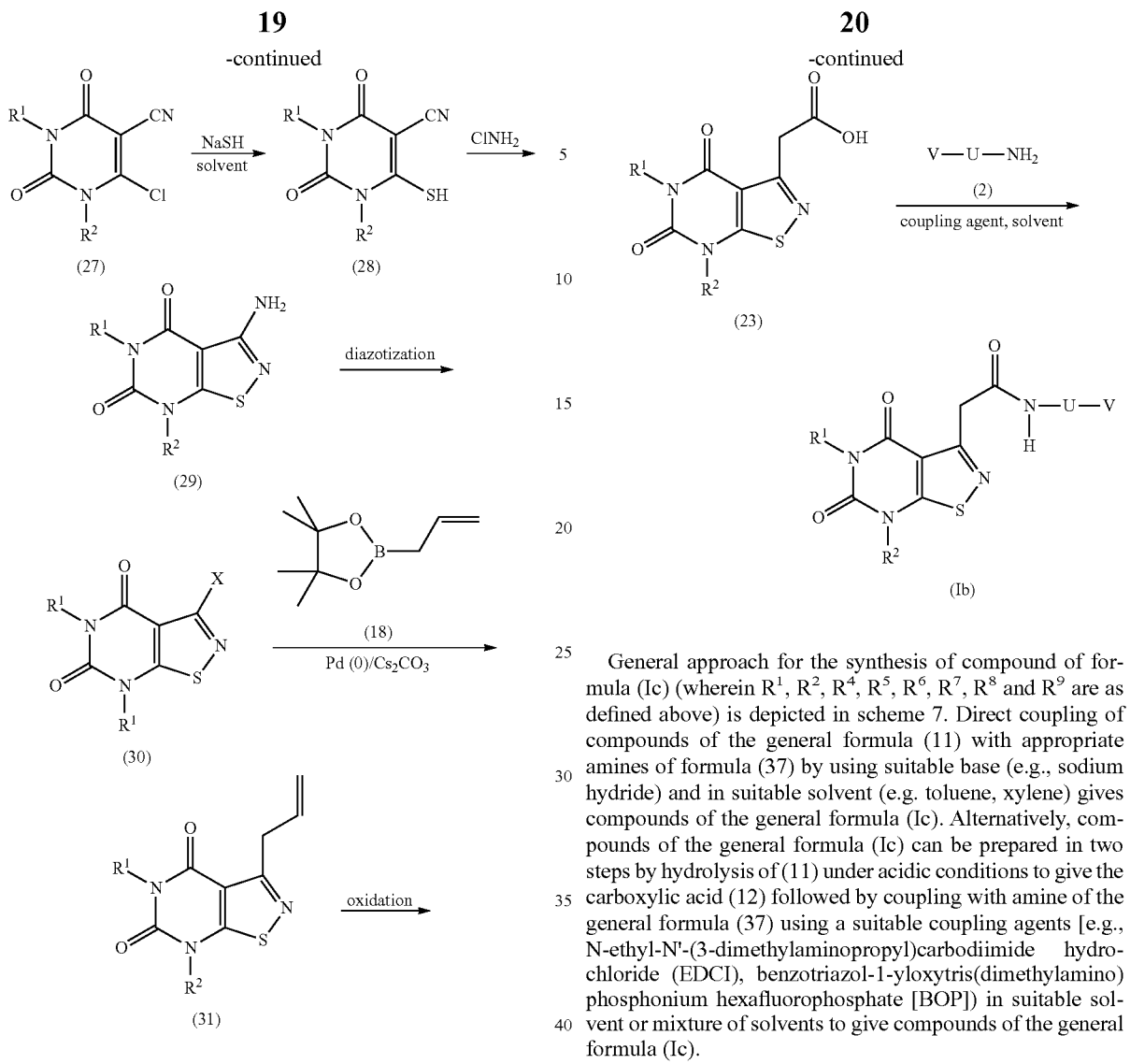

General approach for the synthesis of compound of formula (Ic) (wherein $R^1$, $R^2$, $R^4$, $R^5$, $R^6$, $R^7$, $R^8$ and $R^9$ are as defined above) is depicted in scheme 7. Direct coupling of compounds of the general formula (11) with appropriate amines of formula (37) by using suitable base (e.g., sodium hydride) and in suitable solvent (e.g. toluene, xylene) gives compounds of the general formula (Ic). Alternatively, compounds of the general formula (Ic) can be prepared in two steps by hydrolysis of (11) under acidic conditions to give the carboxylic acid (12) followed by coupling with amine of the general formula (37) using a suitable coupling agents [e.g., N-ethyl-N'-(3-dimethylaminopropyl)carbodiimide hydrochloride (EDCI), benzotriazol-1-yloxytris(dimethylamino) phosphonium hexafluorophosphate [BOP]) in suitable solvent or mixture of solvents to give compounds of the general formula (Ic).

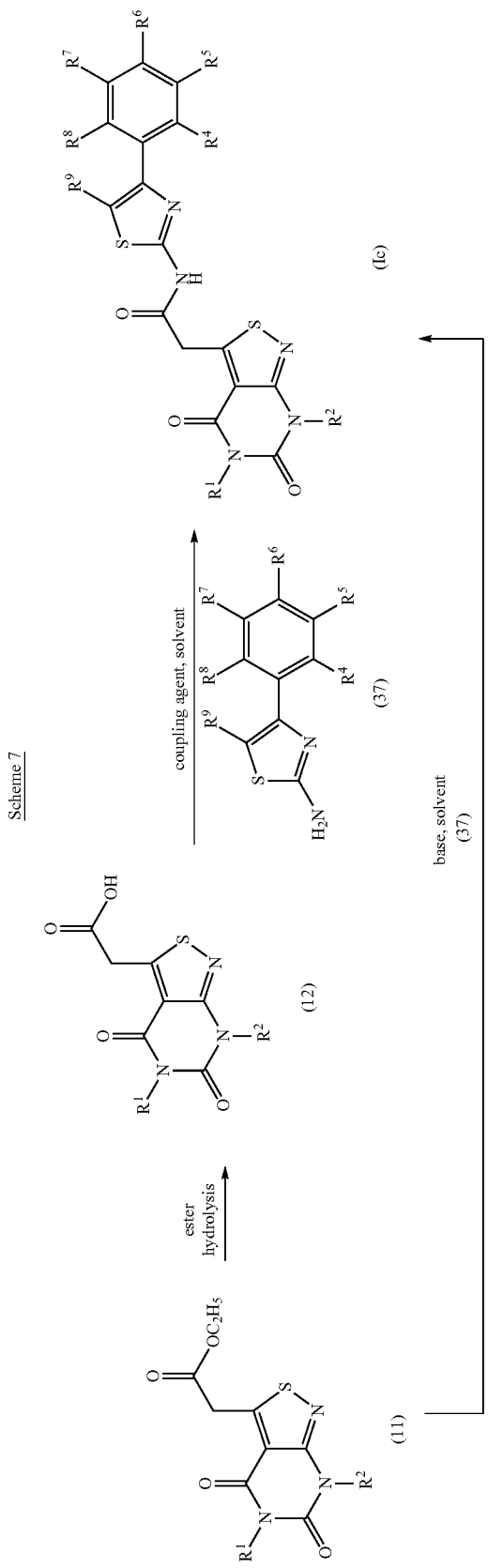

General approach for the synthesis of compound of formula (Id) (wherein $R^1$, $R^2$, $R^4$, $R^5$, $R^6$, $R^7$, $R^8$ and $R^9$ are as defined above) is depicted in scheme 8. Direct coupling of compounds of the general formula (23) with appropriate amines of formula (37) by using suitable coupling agents [e.g., N-ethyl-N'-(3-dimethylaminopropyl)carbodiimide hydrochloride (EDCI), benzotriazol-1-yloxytris(dimethylamino)phosphonium hexafluorophosphate [BOP]) in suitable solvent or mixture of solvents gives compounds of the general formula (Id). Alternatively, compounds of the general formula (Id) can also be prepared in two steps by esterification of (23) to give the corresponding ester of the formula (24) followed by its coupling with amine of the general formula (37) using a suitable base (e.g., sodium hydride) and in suitable solvent (e.g. toluene, xylene) to gives compounds of the general formula (Id).

sponding benzoic acid derivative of formula (32) in three steps. Thus, acid of formula (32) was converted to the corresponding acid chloride of formula (33) using oxalyl chloride in the presence of catalytic amounts of DMF in dry dichloromethane. The acid chloride of formula (33) was converted to corresponding Weinerb amide of formula (35) by treating with N,O-dimethylhydroxylamine hydrochloride of formula (34) in the presence of a suitable base such as triethylamine. The addition of methyl magnesium iodide to Weinreb amide of formula (35) afforded acetophenone derivative of formula (36).

Conversion of acetophenone derivative of formula (36) to 2-amino-4-substituted aryl thiazole of the formula (37) can be effected by two approaches as described in Scheme 9. In the first case acetophenone was converted to the corresponding phenacyl bromide, which in turn was reacted with thiourea in

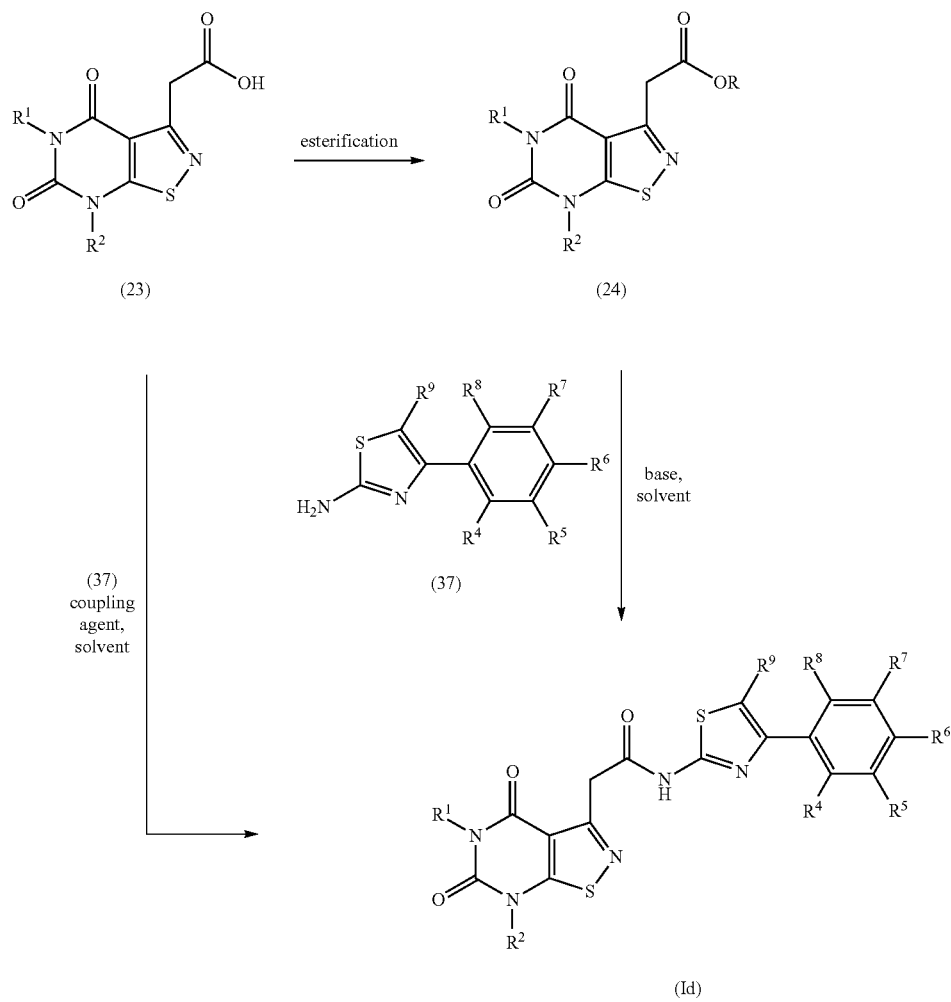

Scheme 9 depicts synthesis of 2-amino-4-aryl thiazoles of the formula (37) (wherein $R^4$, $R^5$, $R^6$, $R^7$, $R^8$ and $R^9$ are as defined above in description) which is prepared from acetophenones of the formula (36) using known approaches. Certain di- and tri-substituted acetophenones were not commercially available and they were prepared from the correa suitable solvent such as tetrahydrofuran at refluxing condition. Alternatively, acetophenone derivative of formula (36) can be converted to 2-amino-4-aryl thiazole (37) in one step by its reaction with thiourea and iodine in refluxing ethanol (Carroll, K. et al. *J. Am. Chem. Soc.,* 1950, 3722 and Naik, S. J.; Halkar, U. P., *ARKIVOC,* 2005, xiii, 141-149).

Scheme 9

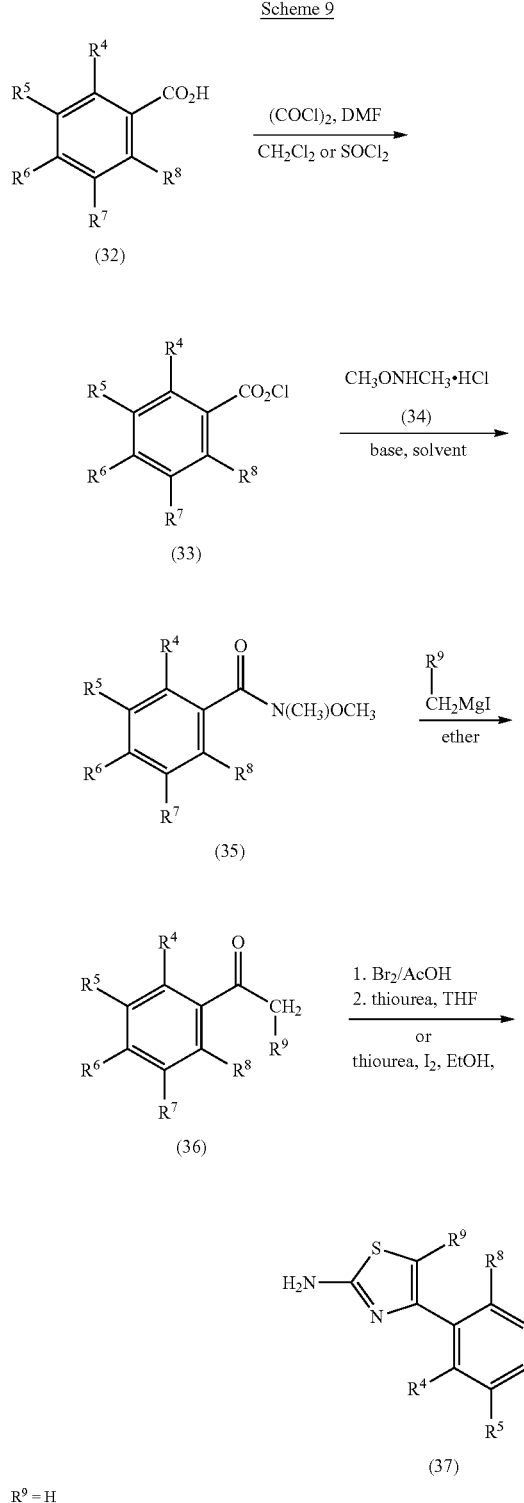

R⁹ = H

3-Amino-1-arylpyrazole was prepared as shown in Scheme 10. Reaction of phenylhydrazine derivative of formula (38) (wherein $R^4$, $R^5$, $R^6$, $R^7$ and $R^8$ are as defined above in description) with acrylonitrile in the presence of a suitable base such as sodium ethoxide or sodium methoxide in refluxing ethanol affords the dihydro derivative of compound of formula (39). Intermediate (39) on oxidation with N-bromosuccinimide as reported by Duffin, G. F. et al, *J. Chem. Soc.*, 1954, 408-415, gives 3-amino-1-arylpyrazoles derivative of formula (40).

Scheme 10

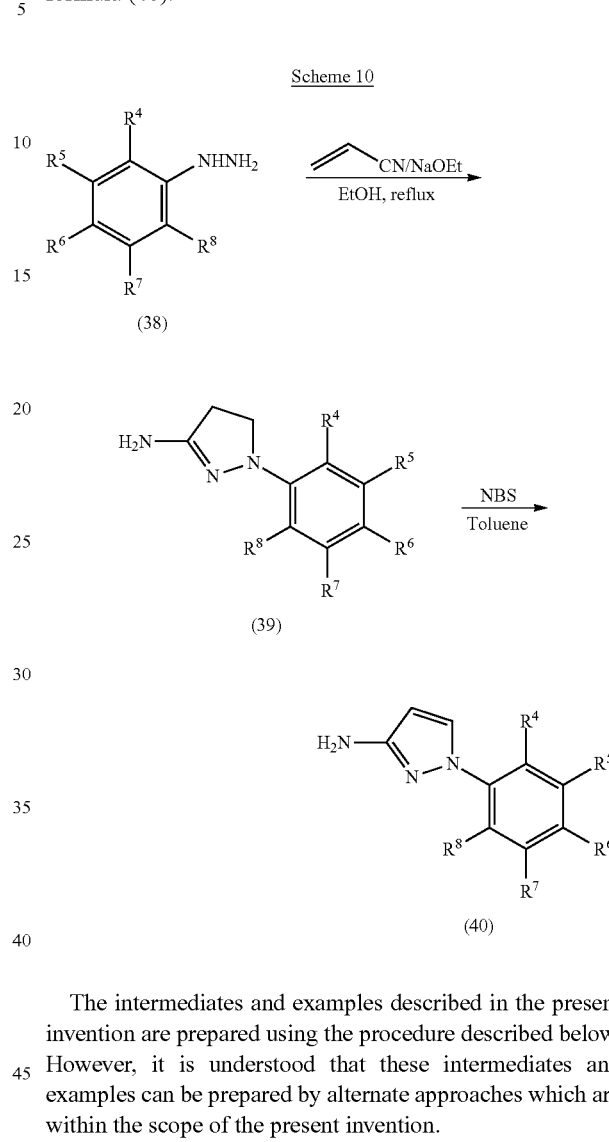

The intermediates and examples described in the present invention are prepared using the procedure described below. However, it is understood that these intermediates and examples can be prepared by alternate approaches which are within the scope of the present invention.

EXPERIMENTAL

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses. The following abbreviations are used in the text: DMSO-$d_6$: Hexadeuterodimethyl sulfoxide; DMF: N,N-dimethylformamide, M.P.: Melting point; J: Coupling constant in units of Hz; RT or rt: room temperature (22-26° C.). Aq.: aqueous AcOEt: ethyl acetate; equiv. or eq.: equivalents.

Intermediates

Intermediate 1

(5,7-Dimethyl-4,6-dioxo-4,5,6,7-tetrahydro[1,2]thiazolo[3,4-d]pyrimidin-3-yl)acetic acid

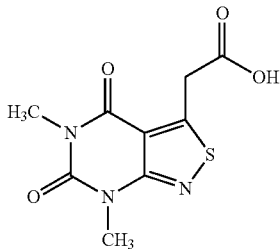 [SMILES: Cn1c(=O)c2c(CC(=O)O)snc2n(C)c1=O]

Step 1:
Methyl 6-amino-1,3-dimethyl-2,4-dioxo-1,2,3,4-tetrahydropyrimidine-5-carbodithioate: To a stirred solution of 6-amino-1,3-dimethyl uracil (50.0 g, 322.24 mmol) in DMSO (488 ml) was added dropwise a solution of 8 N sodium hydroxide (96.6 ml) and carbon disulphide (12.53 ml, 209.45 mmol) at 0° C. The resulting reaction mixture was vigorously stirred at room temperature for 30 min. The reaction mixture was cooled to 0-5° C. and dimethyl sulphate (31 ml, 418 mmol) was added dropwise over a period of 30 min. The reaction mixture was then slowly warmed to room temperature and stirred further for 3 h. The mixture was then diluted with water (500 ml) and precipitated solid was collected by filtration to give 30.2 g of the product as a yellow solid; $^1$H NMR (300 MHz, CF$_3$COOD) δ 2.73 (s, 3H), 3.51 (s, 3H), 3.62 (s, 3H).

Step 2:
5,7-Dimethyl-3-(methylsulfanyl)[1,2]thiazolo[3,4-d]pyrimidine-4,6(5H,7H)-dione: The mixture of step 1 intermediate (15.0 g, 60.64 mmol) and iodine (15.39 g, 60.64 mmol) in dry DMSO (250 ml) was heated at 100° C. for 3 h under nitrogen atmosphere. The mixture was cooled to room temperature and quenched into water (200 ml), solid separated out was filtered and washed with saturated solution of sodium thiosulphate (150 ml), water (100 ml) and dried to obtain 13.4 g as an off white solid; $^1$H NMR (300 MHz, DMSO-d$_6$) δ 2.67 (s, 3H), 3.18 (s, 3H), 3.40 (s, 3H).

Step 3:
5,7-Dimethyl-3-(methylsulfonyl)[1,2]thiazolo[3,4-c]pyrimidine-4,6(5H,7H)-dione: To a stirred solution of Step 2 intermediate (13.0 g, 53.49 mmol) in mixture of acetonitrile and water (1:1, 213.8 ml) was added oxone (98.5 g, 160.49 mmol) and resulting suspension was stirred at room temperature for 24 h. The mixture was filtered and filtrate was concentrated. The residue obtained after evaporation of the solvent was dissolved in chloroform (500 ml), washed with brine (150 ml) and dried over Na$_2$SO$_4$. The evaporation of solvent gave 12.6 g of the product as a white solid; $^1$H NMR (300 MHz, DMSO-d$_6$) δ 3.26 (s, 3H), 3.49 (s, 3H), 3.71 (s, 3H).

Step 4:
Diethyl(5,7-dimethyl-4,6-dioxo-4,5,6,7-tetrahydro[1,2]thiazolo[3,4-d]pyrimidin-3-yl)propanedioate: To a stirred suspension of sodium hydride (60% dispersion in mineral oil, 3.6 g, 90.9 mmol) in dry DMSO (113 ml) was added diethyl malonate (14.56 g, 90.9 mmol) at room temperature under nitrogen atmosphere. After evolution of hydrogen ceased, Step 3 intermediate (12.5 g, 45.45 mmol) was added and heated at 80° C. for 2 h. The reaction mixture was cooled to room temperature, acetic acid was added to pH 5 and the reaction mixture was diluted with cold water (300 ml). Precipitated solid was collected by filtration to give 13.9 g of the product as a white solid; $^1$H NMR (300 MHz, DMSO-d$_6$) δ 1.32 (t, J=7.2 Hz, 6H), 3.40 (s, 3H), 3.64 (s, 3H), 4.24-4.37 (m, 4H), 6.05 (s, 1H).

Step 5:
Ethyl(5,7-dimethyl-4,6-dioxo-4,5,6,7-tetrahydro[1,2]thiazolo[3,4-d]pyrimidin-3-yl)acetate: To a stirred solution of Step 4 intermediate (13.8 g, 38.8 mmol) in dry ethanol (155 ml) was added a catalytic amount of sodium hydride (60% dispersion in mineral oil, 355 mg, 8.87 mmol) at room temperature and the reaction mixture was refluxed for 48 h under nitrogen atmosphere. Excess of solvent was removed under reduced pressure and the residue was cooled in ice bath, 1 N HCl was added slowly to the reaction mixture, solid obtained was collected by filtration and dried to give 9.1 g of the product as a yellow solid; $^1$H NMR (300 MHz, DMSO-d$_6$) δ 1.34 (t, J=6.9 Hz, 3H), 3.40 (s, 3H), 3.63 (s, 3H), 4.30 (q, J=6.9 Hz, 2H), 4.50 (s, 2H)

Step 6:
(5,7-Dimethyl-4,6-dioxo-4,5,6,7-tetrahydro[1,2]thiazolo[3,4-d]pyrimidin-3-yl)acetic acid: The title compound was prepared using above Step 5 intermediate (9.0 g, 31.8 mmol), 6 N H$_2$SO$_4$ (80 ml) and dioxane (80 ml) to give 5.8 g of the product as yellow solid; $^1$H NMR (300 MHz, DMSO-d$_6$) δ 3.22 (s, 3H), 3.46 (s, 3H), 4.51 (s, 2H), 13.45 (br s, 1H).

Intermediate 2

(5,7-Dimethyl-4,6-dioxo-4,5,6,7-tetrahydro[1,2]thiazolo[5,4-d]pyrimidin-3-yl)acetic acid

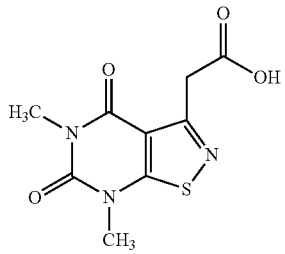 [SMILES: Cn1c(=O)c2c(CC(=O)O)nsc2n(C)c1=O]

Step 1:
6-Chloro-1,3-dimethylpyrimidine-2,4(1H,3H)-dione: To a stirred solution of 1,3-dimethylbarbituric acid (20.0 g, 128.09 mmol) in water (10 ml), phosphorous oxychloride (80 ml) was added slowly by externally cooling and reaction was then refluxed for 3 h. The reaction mixture was allowed to cool to 0° C. and quenched with ice cold water (350 ml). The reaction mixture was extracted with chloroform (2×200 ml) and the combined organic extracts were washed with water, dried over Na$_2$SO$_4$ and concentrated to obtain 21.0 g of the product as a pale brown solid; $^1$H NMR (300 MHz, CDCl$_3$) δ 3.33 (s, 3H), 3.57 (s, 3H), 5.94 (s, 1H).

Step 2:
6-Mercapto-1,3-dimethylpyrimidine-2,4(1H,3H)-dione:
A solution of sodium hydrosulphide hydrate (74.77 g, 1335.243 mmol) in water (125 ml) was added dropwise to a stirred solution of Step 1 (50.0 g, 286.532 mmol) in chloroform (250 ml) and ethanol (636 ml) in an ice water bath, and the mixture was stirred at room temperature overnight. The reaction mixture was evaporated to dryness in vacuo at room temperature. The residue obtained was dissolved in water (100 ml) and extracted with dichloromethane (2×100 ml). The aqueous layer was acidified with 1 N HCl. Precipitated solid was filtered, washed with water (2×100 ml) and dried to obtain 49.22 g of the product as a pale yellow solid; $^1$H NMR (300 MHz, CDCl$_3$) δ 3.33 (s, 3H), 3.74 (s, 3H), 4.17 (s, 2H).

Step 3:

5-Hydroxy-1,3-dimethyl-2H-thiopyrano[2,3-d]pyrimidine-2,4,7(1H,3H)-trione: A mixture of Step 2 intermediate (12.75 g, 74.127 mmol), malonic acid (9.30 g, 88.953 mmol), acetic acid (7.41 ml) and acetic anhydride (16.8 ml) was heated to 80° C. under nitrogen atmosphere for 2 h. The reaction mixture was cooled to room temperature and quenched with water (50 ml). Precipitated solid was filtered, washed with water (2×50 ml) and dried well to obtain 14.4 g of the product as brown solid; $^1$H NMR (300 MHz, DMSO-d$_6$) δ 3.28 (s, 3H), 3.48 (s, 3H), 5.73 (s, 1H), 13.76 (br s, 1H).

Step 4:

(5,7-Dimethyl-4,6-dioxo-4,5,6,7-tetrahydroisothiazolo[3,4-d]pyrimidin-3-yl)acetic acid: A mixture of Step 3 intermediate (14.4 g, 60.00 mmol), hydroxylamine hydrochloride (14.6 g, 210.00 mmol) and triethylamine (30.4 ml, 216.00 mmol) in dry methanol (150 ml) were heated at reflux under nitrogen atmosphere for about 48 h, The residue obtained after evaporation to dryness was dissolved in saturated solution of sodium bicarbonate and extracted with ethyl acetate. After acidification of aqueous phase the product was extracted with chloroform (3×100 ml). The combined organic layers were dried (Na$_2$SO$_4$) and concentrated. The residue obtained was triturated with acetone (20 ml). Precipitated solid was collected by filtration to obtain 2.58 g of product as a pale yellow solid; $^1$H NMR (300 MHz, DMSO-d$_6$) δ 3.22 (s, 3H), 3.46 (s, 3H), 3.96 (s, 2H), 12.57 (br s, 1H).

Intermediate 3

Ethyl(5,7-dimethyl-4,6-dioxo-4,5,6,7-tetrahydro[1,2]thiazolo[5,4-d]pyrimidin-3-yl)acetate

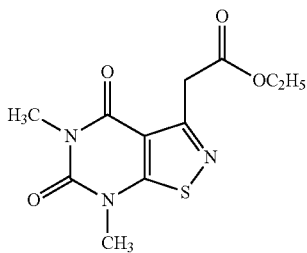 [SMILES: CCOC(=O)Cc1nsc2c1c(=O)n(C)c(=O)n2C]

A mixture of Intermediate 2 (2.00 g, 7.835 mmol) and concentrated sulphuric acid (0.5 ml) in dry ethanol (20.0 ml) was refluxed for 4 h. The solvent was evaporated completely under reduced pressure and residue obtained was diluted with water (50 ml). Precipitated solid was filtered, washed with water (3×50 ml), dried well to give 1.75 g of the product as a off white solid; $^1$H NMR (300 MHz, CDCl$_3$) δ 1.28 (t, J=7.2 Hz, 3H), 3.39 (s, 3H), 3.56 (s, 3H), 4.12 (s, 2H), 4.21 (q, J=6.9 Hz, 2H).

General Procedure for the Preparation of 2-Amino-4-Aryl Thiazoles

Method 1

A solution of acetophenone derivative (1.0 equiv.) in glacial acetic acid (5 vol) was added liquid bromine (1.0 equiv.) at 0° C. and reaction mixture was stirred at room temperature for 2 h. The reaction mixture was diluted with water and extracted with ethyl acetate, washed with brine and dried over Na$_2$SO$_4$. The crude product obtained upon concentration was dissolved in dry THF (10 vol) and thiourea (2.0 equiv.) was added and refluxed for overnight. The reaction mixture was diluted with ethyl acetate, washed with sodium thiosulfate solution and organic layer was treated with 1N HCl to result salt formation of the amine. The precipitated salt was collected by filtration. The salt was then treated with saturated solution of NaHCO$_3$ to re-generate the amine. The mixture was extracted with dichloromethane (2×50 ml) and the combined organic extracts were washed with water and brine. The solvent was evaporated under reduced pressure to afford the 2-amino-4-aryl-thiazole derivative.

Method 2

A solution of acetophenone derivative (1.0 equiv.), thiourea (2.0 equiv.) and iodine (1.0 equiv.) in dry ethanol (5 vol) was refluxed for 24 h. The reaction mixture was diluted with ethyl acetate and the layers were separated. The organic layer was washed with sodium thiosulfate solution to remove iodine. The ethyl acetate solution was treated with 1N HCl and precipitated salt was collected by filtration. The free amine was re-generated as described in Method 1 given above.

All the 2-amino-4-aryl-thiazole derivatives were prepared by either Method 1 or Method 2 starting from appropriate aryl alkyl ketones. Structure information and characterization data for selected intermediates are given in Table 1.

TABLE 1

Structural details and $^1$H NMR data of selected 2-aminothiazole intermediates

| S N. | Structure | Mol. Formula (Mol. Wt.) | $^1$H NMR (δ ppm, 300 MHz) |
|---|---|---|---|
| 1. | 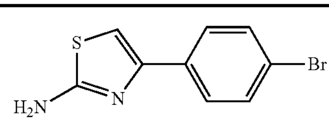 | C$_9$H$_7$BrN$_2$S 255.14 | DMSO-d$_6$: 7.61(d, J = 8.1, 2H); 7.46 (d, J = 7.8, 2H); 6.70(s, 1H); 4.99 (br. s, 2H). |

TABLE 1-continued

Structural details and $^1$H NMR data of selected 2-aminothiazole intermediates

| S N. | Structure | Mol. Formula (Mol. Wt.) | $^1$H NMR (δ ppm, 300 MHz) |
|---|---|---|---|
| 2. | (4-chlorophenyl-thiazol-2-amine) | $C_9H_7ClN_2S$ 210.68 | DMSO-$d_6$: 7.78(d, J = 8.4, 2H); 7.39 (d, J = 7.8, 2H); 7.07(br. s, 2H); 7.05 (s, 1H). |
| 3. | (3-trifluoromethylphenyl-thiazol-2-amine) | $C_{10}H_7F_3N_2S$ 244.24 | CDCl$_3$: 8.12-8.06(m, 1H); 7.91(d, J = 6.9, 1H); 7.50-7.42(m, 2H); 6.79 (s, 1H); 5.02(br. s, 2H). |
| 4. | (4-tert-butylphenyl-thiazol-2-amine) | $C_{13}H_{16}N_2S$ 232.35 | DMSO-$d_6$: 1.28(s, 9H), 6.89(s, 1H), 7.01(br.s, 2H); 7.34(d, J = 9.0 Hz, 2H), 7.67(d, J = 8.1 Hz, 2H) |
| 5. | (4-ethylphenyl-thiazol-2-amine) | $C_{11}H_{12}N_2S$ (220.07) | CDCl$_3$: 7.66(d, J = 7.8, 2H); 7.20(d, J = 7.5, 2H); 6.65(s, 1H); 5.06(br. s, 2H); 2.65(d, J = 7.5, 2H); 1.24(t, J = 7.2, 3H). |
| 6. | (4-cyclohexylphenyl-thiazol-2-amine) | $C_{15}H_{18}N_2S$ (258.38) | CDCl$_3$: 7.65(d, J = 7.8, 2H); 7.18(d, J = 7.8, 2H); 6.63(s, 1H); 5.12(br.s, 2H); 2.52-2.45(m, 1H); 1.90-1.80(m, 6H); 1.45-1.38(m, 4H). |
| 7. | (4-trifluoromethoxyphenyl-thiazol-2-amine) | $C_{13}H_{16}N_2S$ 260.24 | CDCl$_3$: 7.09(s, 1H), 7.13(br.s, 2H), 7.35(d, J = 8.4, 2H); 7.90(d, J = 8.1, 2H). |
| 8. | (3,5-dichlorophenyl-thiazol-2-amine) | $C_9H_6Cl_2N_2S$ 245.13 | DMSO-$d_6$: 7.80(s, 2H); 7.46-7.40(m, 1H); 7.31(s, 1H); 7.17(br. s, 2H). |
| 9. | (3,4-dichlorophenyl-thiazol-2-amine) | $C_9H_6Cl_2N_2S$ 245.13 | CDCl$_3$: 7.85(s, 1H); 7.56(dd, J = 8.4, 2.1, 1H); 7.39(d, J = 8.4, 1H); 6.72 (s, 1H); 5.01(br.s, 2H). |
| 10. | (3,4-difluorophenyl-thiazol-2-amine) | $C_9H_6F_2N_2S$ (212.22) | CDCl$_3$: 7.60-7.53(m, 1H); 7.48-7.43 (m, 1H); 7.18-7.07(m, 1H); 6.66(s, 1H); 4.98(br. s, 2H). |
| 11. | (2,4-difluorophenyl-thiazol-2-amine) | $C_9H_6F_2N_2S$ 212.22 | CDCl$_3$: 5.04(br. s, 2H), 6.80-6.93(m, 3H), 7.95-8.04(m, 1H) |
| 12. | (3-fluoro-4-trifluoromethylphenyl-thiazol-2-amine) | $C_{12}H_6F_4N_2S$ 262.23 | DMSO-$d_6$: 7.87-7.74(m, 3H); 7.40(s, 1H); 7.22(br. s, 2H). |

TABLE 1-continued

Structural details and ¹H NMR data of selected 2-aminothiazole intermediates

| S N. | Structure | Mol. Formula (Mol. Wt.) | ¹H NMR (δ ppm, 300 MHz) |
|---|---|---|---|
| 13. | 2-amino-4-(4-fluoro-3-trifluoromethylphenyl)thiazole | $C_{10}H_6F_4N_2S$ 262.23 | DMSO-$d_6$: 7.20(br. s, 2H), 7.24(s, 1H), 7.52(t, J = 8.7 Hz, 1H), 8.13(d, J = 6.0 Hz, 2H) |
| 14. | 2-amino-4-(2-fluoro-3-trifluoromethylphenyl)thiazole | $C_{10}H_6F_4N_2S$ 262.23 | CDCl$_3$: 5.04(br s, 2H), 7.10(s, 1H), 7.27(t, J = 7.5 Hz, 1H), 7.51(t, J = 6.9 Hz, 1H), 8.21-8.28(m, 1H) |
| 15. | 2-amino-4-(2-fluoro-4-trifluoromethylphenyl)thiazole | $C_{10}H_6F_4N_2S$ 262.23 | CDCl$_3$: 5.00(br s, 2H); 7.16(s, 1H); 7.37(d, J = 11.7, 1H); 7.44(d, J = 8.4, 1H); 8.18(t, J = 7.8, 1H). |
| 16. | 2-amino-4-(3-trifluoromethyl-5-fluorophenyl)thiazole | $C_{10}H_6F_4N_2S$ 262.23 | DMSO-$d_6$: 7.23(br s, 2H); 7.41(s, 1H); 7.55(d, J = 9.0, 1H); 7.89(d, J = 10.2, 1H); 7.99(s, 2H). |
| 17. | 2-amino-4-(4-chloro-3-trifluoromethylphenyl)thiazole | $C_{10}H_6ClF_3N_2S$ 278.68 | CDCl$_3$: 5.05(br s, 2H), 6.78(s, 1H), 7.46(d, J = 8.1 Hz, 1H), 7.82(d, J = 7.8 Hz, 1H), 8.08(s, 1H) |
| 18. | 2-amino-4-(4-fluoro-3-trifluoromethoxyphenyl)thiazole | $C_{10}H_6F_4N_2OS$ 278.23 | DMSO-$d_6$: 7.92-7.85(m, 2H); 7.50(t, J = 8.7 Hz, 1H); 7.18(br. s, 3H). |
| 19. | 2-amino-4-(4-trifluoromethoxy-3-fluorophenyl)thiazole | $C_{10}H_6F_4N_2OS$ 278.23 | DMSO-$d_6$: 7.87-7.80(m, 1H); 7.73 (d, J = 8.7 Hz, 1H); 7.55(d, J = 8.1 Hz, 1H); 7.24(s, 1H); 7.18(br.s, 2H). |
| 20. | 2-amino-4-(4-chloro-3-trifluoromethylphenyl)thiazole | $C_{10}H_6ClF_3N_2S$ (278.68) | CDCl$_3$: 8.08(s, 1H); 7.82(d, J = 7.8, 1H); 7.46(d, J = 8.1, 1H); 6.78(s, 1H); 5.05(br. s, 2H). |
| 21. | 2-amino-4-(4-trifluoromethoxy-3-chlorophenyl)thiazole | $C_{10}H_6ClF_3N_2OS$ 294.68 | DMSO-$d_6$: 7.19(br s, 2H), 7.57(, J = 8.1 Hz, 1H), 7.86(d, J = 8.1 Hz, 1H), 8.05(s, 1H) |
| 22. | 2-amino-4-(4-chloro-3-trifluoromethoxyphenyl)thiazole | $C_{10}H_6ClF_3N_2OS$ 294.68 | DMSO-$d_6$: 7.22(br s, 2H), 7.28(s, 1H), 7.68(d, J = 8.4 Hz, 1H), 7.83-7.92(m, 2H) |

TABLE 1-continued

Structural details and ¹H NMR data of selected 2-aminothiazole intermediates

| S N. | Structure | Mol. Formula (Mol. Wt.) | ¹H NMR (δ ppm, 300 MHz) |
|---|---|---|---|
| 23. | (3-CF₃, 5-Cl phenyl)-2-aminothiazole | $C_{10}H_6ClF_3N_2S$ 278.68 | DMSO-$d_6$: 8.17(br s, 2H), 7.46(s, 1H), 7.73(s, 1H), 8.10(s, 1H), 8.17 (s, 1H) |
| 24. | (3,5-difluoro-4-OCHF₂ phenyl)-2-aminothiazole | $C_{10}H_6F_4N_2OS$ (278.23) | DMSO-$d_6$: 7.20(br. s, 2H), 7.24(t, J = 72.3 Hz, 1H), 7.48(s, 1H), 7.65(d, J = 9.0, 2H) |
| 25. | (3,5-difluoro-4-CF₃ phenyl)-2-aminothiazole | $C_{10}H_5F_5N_2S$ 280.22 | DMSO-$d_6$: 7.72(d, J = 11.7, 2H); 7.52(s, 1H); 7.29(br. s, 2H). |
| 26. | (2,4-difluoro-3-CF₃ phenyl)-2-aminothiazole | $C_{10}H_5F_5N_2S$ 280.22 | DMSO-$d_6$: 8.35-8.21(m, 1H); 7.48-7.35(m, 1H); 7.21(br. s, 2H); 7.05(s, 1H). |
| 27. | (2,3-difluoro-4-CF₃ phenyl)-2-aminothiazole | $C_{10}H_5F_5N_2S$ 280.22 | DMSO-$d_6$: 7.24(s, 1H), 7.28(br. s, 2H), 7.65(t, J = 7.2, 1H), 7.94(t, J = 7.5, 1H). |
| 28. | (2-fluoro-5-CF₃ phenyl)-2-aminothiazole | $C_{10}H_6F_4N_2S$ 262.23 | CDCl₃: 8.36-8.29(m, 1H); 7.73-7.65 (m, 1H); 7.58-7.50(m, 1H); 7.26 (br.s, 2H); 7.13(s, 1H) |
| 29 | (3-Cl, 4-CF₃ phenyl)-2-aminothiazole | $C_{10}H_6ClF_3N_2S$ 278.68 | DMSO-$d_6$: 7.25(br s, 2H), 7.43(s, 1H), 7.84(d, J = 8.4 Hz, 1H), 7.94 (d, J = 8.4 Hz, 1H), 8.09(s, 1H) |
| 30 | (2,4-dichloro-5-fluoro phenyl)-2-aminothiazole | $C_9H_5Cl_2FN_2S$ (263.12) | CDCl₃: 4.97(br s, 2H), 7.19(s, 1H), 7.44(d, J = 6.9 Hz, 1H), 7.74(d, J = 9.0 Hz, 1H) |
| 31 | (3-fluoro-4-OCHF₂ phenyl)-2-aminothiazole | $C_{10}H_7F_3N_2OS$ (260.24) | DMSO-$d_6$: 7.75-7.62(m, 2H); 7.33(t, J = 8.1, 1H); 7.23(t, J = 73.2, 1H); 7.12(br.s, 3H). |

Further it should also be noted that several fluoro substituted 2-amino-4-aryl thiazoles can be prepared using the approach described in Scheme 9 by following Method 1 or Method 2 starting from appropriate fluorinated benzoic acid or fluoroninated acetophenone. A few examples of such aminothiazole intermediates are given in Table 2.

TABLE 2

Structure of fluoro substituted 2-amino-4-arylthiazoles

| S No | Structure | Name | Mol. Formula | (Mol. Wt.) |
|---|---|---|---|---|
| 1. | 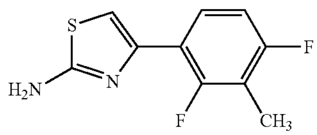 | 4-[(2,4-difluoro-3-methyl)phenyl]-1,3-thiaozl-2-amine | $C_{10}H_8F_2N_2S$ | 226.25 |
| 2. | 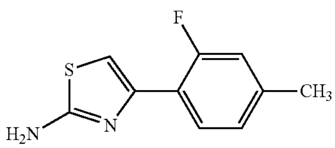 | 4-[(2-fluoro-4-methyl)phenyl]-1,3-thiazol-2-amine | $C_{10}H_9FN_2S$ | 208.26 |
| 3. | 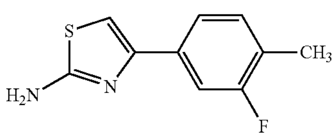 | 4-[(3-fluoro-4-methyl)phenyl]-1,3-thiazol-2-amine | $C_{10}H_9FN_2S$ | 208.26 |

Preparation of 1-(4-Bromophenyl)-1H-pyrazol-3-amine

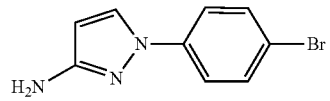

The title compound was prepared by the reaction of 4-bromophenylhydrazine with acrylonitrile in the presence of a suitable base such as sodium ethoxide in refluxing ethanol followed by oxidation with N-bromosuccinimide; $^1$H NMR (300 MHz, DMSO-$d_6$) δ 3.81 (br s, 2H), 5.84 (s, 1H), 7.41 (d, J=8.7 Hz, 2H), 7.47 (d, J=8.7 Hz, 2H), 7.63 (s, 1H).

3-(4-Chlorophenyl)isoxazol-5-amine, 3-(4-chlorophenyl)-1H-pyrazol-5-amine and 5-(4-bromophenyl)-1,3,4-thiadiazol-2-amine were used in the synthesis were purchased from Aldrich.

The illustrative examples described herein were synthesized by coupling Intermediate 1-3 with appropriate aryl amines.

EXAMPLES

General Procedure for the Preparation of Examples

Method A

To a stirred solution of carboxylic acid derivative (1.0 equiv.) in 1,2-dichloroethane was added EDCI (1.2 equiv.), HOBt (0.3 equiv.) and 4-dimethylaminopyridine (0.1 equiv.) and the mixture was stirred at room temperature for 10-15 min. An appropriate amine (1.0 equiv.) was then added and mixture was stirred under nitrogen atmosphere at the same temperature for 48 h or heated at reflux temperature for 24 h. The solvent was evaporated under reduced pressure and the residue obtained was diluted with methanol and stirred at room temperature for 30 min. The solid separated out was collected by filtration. The solid product was further purified by recrystalisation from isopropanol or methanol to give the desired products.

Method B

To a stirred solution of appropriate thiazole amine (1.2 equiv.) in dry toluene was added sodium hydride and the mixture was stirred at room temperature for 30 min. Isothiazole acetic acid ester (1.0 equiv.) was added and the mixture was heated to reflux under nitrogen atmosphere for 24 h. The mixture was cooled and acidified to pH 6.0 by addition of 2 N hydrochloric acid. The solid precipitated out was collected by filtration. The product was further purified by crystallization or by silica gel column chromatography using a mixture of methanol and chloroform.

Example 1

2-(5,7-Dimethyl-4,6-dioxo-4,5,6,7-tetrahydro[1,2]thiazolo[3,4-d]pyrimidin-3-yl)-N-{4-[3-(trifluoromethyl)phenyl]-1,3-thiazol-2-yl}acetamide

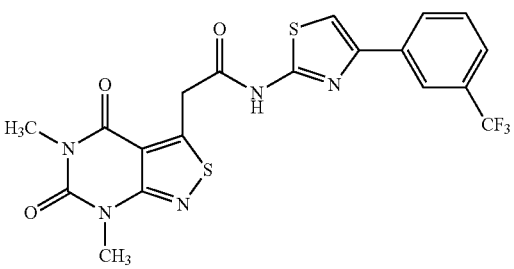 [SMILES: Cn1c(=O)c2c(CC(=O)Nc3nc(-c4cccc(C(F)(F)F)c4)cs3)snc2n(C)c1=O]

The title compound was prepared according to the general procedure (Method A) by coupling Intermediate 1 (200 mg, 0.784 mmol) with 4-[3-(trifluoromethyl)phenyl]-1,3-thiazol-2-amine (191 mg, 0.784 mmol) in the presence of EDCI hydrochloride (180 mg, 0.940 mmol), HOBt (32 mg, 0.235 mmol) and DMAP (9.5 mg, 0.078 mmol) in 1,2-dichloroethane (8 ml) at reflux temperature to give 50 mg of the product as an off-white solid; $^1$H NMR (300 MHz, DMSO-$d_6$) δ 3.23 (s, 3H), 3.48 (s, 3H), 4.82 (s, 2H), 7.67-7.72 (m, 2H), 7.96 (s, 1H), 8.20-8.26 (m, 2H), 12.93 (br s, 1H); APCI-MS (m/z) 482.07 (M+H)$^+$.

Example 2

N-[4-(4-Chlorophenyl)-1,3-thiazol-2-yl]-2-(5,7-dimethyl-4,6-dioxo-4,5,6,7-tetrahydro[1,2]thiazolo[3,4-d]pyrimidin-3-yl)acetamide

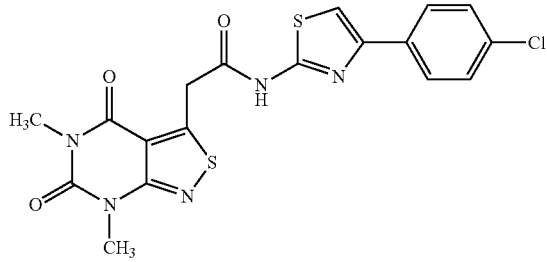 [SMILES: Cn1c(=O)c2c(CC(=O)Nc3nc(-c4ccc(Cl)cc4)cs3)snc2n(C)c1=O]

The title compound was prepared according to the general procedure (Method A) by coupling Intermediate 1 (200 mg, 0.784 mmol) with 4-[4-chlorophenyl]-1,3-thiazol-2-amine (165 mg, 0.784 mmol) in the presence of EDCI hydrochloride (180 mg, 0.940 mmol), HOBt (32 mg, 0.235 mmol) and DMAP (9.5 mg, 0.078 mmol) in 1,2-dichloroethane (8 ml) at reflux temperature to give 25 mg of the product as an off-white solid; $^1$H NMR (300 MHz, DMSO-$d_6$) δ 3.23 (s, 3H), 3.48 (s, 3H), 4.82 (s, 2H), 7.50 (d, J=8.4, 2H), 7.76 (s, 1H), 7.93 (d, J=8.4, 2H), 12.88 (br s, 1H); APCI-MS (m/z) 448.14 (M+H)$^+$.

Example 3

2-(5,7-Dimethyl-4,6-dioxo-4,5,6,7-tetrahydro[1,2]thiazolo[3,4-d]pyrimidin-3-yl)-N-{4-[4-fluoro-3-(trifluoromethoxy)phenyl]-1,3-thiazol-2-yl}acetamide

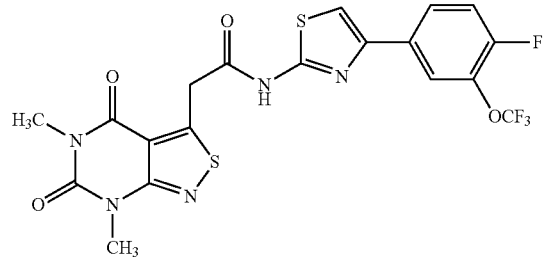 [SMILES: Cn1c(=O)c2c(CC(=O)Nc3nc(-c4ccc(F)c(OC(F)(F)F)c4)cs3)snc2n(C)c1=O]

The title compound was prepared according to the general procedure (Method A) by coupling Intermediate 1 (200 mg, 0.784 mmol) with 4-(4-fluoro-3-(trifluoromethoxy)phenyl)-1,3-thiazol-2-amine (218 mg, 0.784 mmol) in the presence of EDCI hydrochloride (180 mg, 0.940 mmol), HOBt (32 mg, 0.235 mmol) and DMAP (9.5 mg, 0.078 mmol) in 1,2-dichloroethane (8 ml) at reflux temperature to give 53 mg of the product as an off-white solid; $^1$H NMR (300 MHz, DMSO-$d_6$) δ 3.23 (s, 3H), 3.48 (s, 3H), 4.82 (s, 2H), 7.61 (t, J=9.0 Hz, 1H), 7.88 (s, 1H), 8.00-8.06 (m, 2H), 12.91 (br s, 1H); APCI-MS (m/z) 516.07 (M+H)$^+$.

Example 4

2-(5,7-Dimethyl-4,6-dioxo-4,5,6,7-tetrahydro[1,2]thiazolo[3,4-d]pyrimidin-3-yl)-N-{4-[3-fluoro-4-(trifluoromethyl)phenyl]-1,3-thiazol-2-yl}acetamide

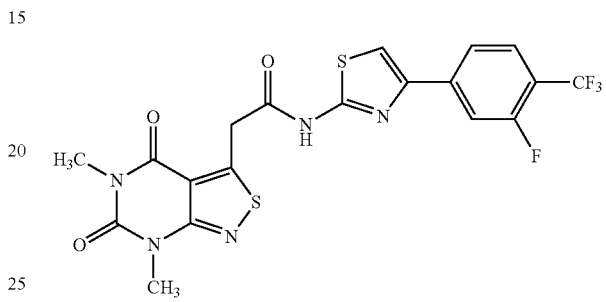

The title compound was prepared according to the general procedure (Method A) by coupling Intermediate 1 (200 mg, 0.784 mmol) with 4-(3-fluoro-4-(trifluoromethyl)phenyl)-1,3-thiazol-2-amine (205 mg, 0.784 mmol) in the presence of EDCI hydrochloride (180 mg, 0.940 mmol), HOBt (32 mg, 0.235 mmol) and DMAP (9.5 mg, 0.078 mmol) in 1,2-dichloroethane (8.3 ml) at reflux temperature to give 18 mg of the product as an off-white solid; $^1$H NMR (300 MHz, DMSO-$d_6$) δ 3.23 (s, 3H), 3.48 (s, 3H), 4.83 (s, 2H), 7.86-8.07 (m, 4H), 12.96 (br s, 1H); APCI-MS (m/z) 500.06 (M+H)$^+$.

Example 5

2-(5,7-Dimethyl-4,6-dioxo-4,5,6,7-tetrahydro[1,2]thiazolo[3,4-d]pyrimidin-3-yl)-N-{4-[2-fluoro-3-(trifluoromethyl)phenyl]-1,3-thiazol-2-yl}acetamide

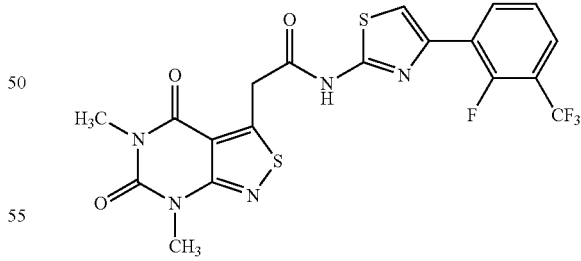

The title compound was prepared according to the general procedure (Method A) by coupling Intermediate 1 (146 mg, 0.572 mmol) with 4-[2-fluoro-3-(trifluoromethyl)phenyl]-1,3-thiazol-2-amine (150 mg, 0.572 mmol) in the presence of EDCI hydrochloride (131 mg, 0.687 mmol), HOBt (23 mg, 0.171 mmol) and DMAP (7 mg, 0.057 mmol) in 1,2-dichloroethane (6 ml) at room temperature to give 31 mg of the product as an off-white solid; $^1$H NMR (300 MHz, DMSO-$d_6$) δ 3.23 (s, 3H), 3.48 (s, 3H), 4.83 (s, 2H), 7.57 (t, J=8.1, 1H), 7.73-7.79 (m, 2H), 8.30-8.36 (m, 1H), 12.95 (br s, 1H); APCI-MS (m/z) 498.10 (M–H)⁻.

Example 6

2-(5,7-Dimethyl-4,6-dioxo-4,5,6,7-tetrahydro[1,2]thiazolo[3,4-c]pyrimidin-3-yl)-N-{4-[4-chloro-3-(trifluoromethyl)phenyl]-1,3-thiazol-2-yl}acetamide

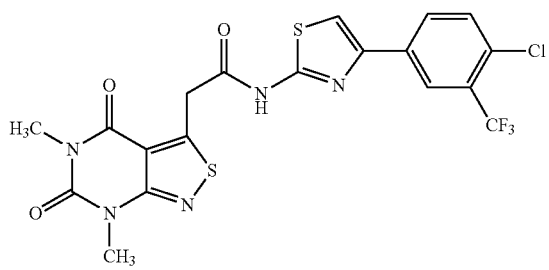 [SMILES: Cn1c(=O)c2c(CC(=O)Nc3nc(-c4ccc(Cl)c(C(F)(F)F)c4)cs3)snc2n(C)c1=O]

The title compound was prepared according to the general procedure (Method A) by coupling Intermediate 1 (200 mg, 0.784 mmol) with 4-[4-chloro-3-(trifluoromethyl)phenyl]-1,3-thiazol-2-amine (218 mg, 0.784 mmol) in the presence of EDCI hydrochloride (180 mg, 0.941 mmol), HOBt (31 mg, 0.235 mmol) and DMAP (9.5 mg, 0.0784 mmol) in 1,2-dichloroethane (8 ml) at room temperature to give 50 mg of the product as an off-white solid; $^1$H NMR (300 MHz, DMSO-$d_6$) δ 3.23 (s, 3H), 3.47 (s, 3H), 4.81 (s, 2H), 7.80-7.835 (m, 1H), 8.00 (s, 1H), 8.17-8.24 (m, 1H), 8.34 (s, 1H), 12.94 (br s, 1H); APCI-MS (m/z) 516.11 (M+H)⁺.

Example 7

2-(5,7-Dimethyl-4,6-dioxo-4,5,6,7-tetrahydro[1,2]thiazolo[3,4-c]pyrimidin-3-yl)-N-{4-[3-fluoro-4-(trifluoromethoxy)phenyl]-1,3-thiazol-2-yl}acetamide

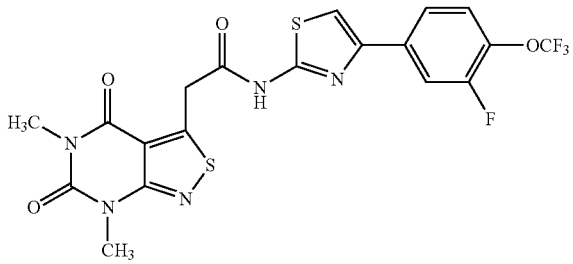 [SMILES: Cn1c(=O)c2c(CC(=O)Nc3nc(-c4ccc(OC(F)(F)F)c(F)c4)cs3)snc2n(C)c1=O]

The title compound was prepared according to the general procedure (Method A) by coupling Intermediate 1 (300 mg, 1.176 mmol) with 4-(3-fluoro-4-(trifluoromethoxy)phenyl)-1,3-thiazol-2-amine (326 mg, 1.176 mmol) in the presence of EDCI hydrochloride (269 mg, 1.411 mmol), HOBt (47 mg, 0.352 mmol) and DMAP (14 mg, 0.117 mmol) in 1,2-dichloroethane (6 ml) at reflux temperature to give 230 mg of the product as an pale yellow solid; $^1$H NMR (300 MHz, DMSO-$d_6$) δ 3.23 (s, 3H), 3.47 (s, 3H), 4.80 (s, 2H), 7.64 (t, J=8.4, 1H), 7.84-8.05 (m, 3H), 12.90 (br s, 1H); APCI-MS (m/z) 516.14 (M+H)⁺.

Example 8

N-[4-(3,4-Dichlorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide

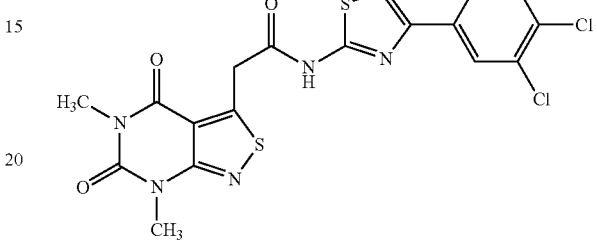

The title compound was prepared according to the general procedure (Method A) by coupling Intermediate 1 (200 mg, 0.784 mmol) with 4-(3,4-dichlorophenyl)-1,3-thiazol-2-amine (192 mg, 0.784 mmol) in the presence of EDCI hydrochloride (180.4 mg, 0.941 mmol), HOBt (31 mg, 0.235 mmol) and DMAP (9.5 mg, 0.078 mmol) in 1,2-dichloroethane (7.8 ml) at reflux temperature to give 23 mg of the product as an pale yellow solid; $^1$H NMR (300 MHz, DMSO-$d_6$) δ 3.23 (s, 3H), 3.47 (s, 3H), 4.81 (s, 2H), 7.70-7.75 (m, 1H), 7.86-7.92 (m, 2H), 8.10-8.16 (m, 1H), 12.88 (br s, 1H); APCI-MS (m/z) 482.13 (M+H)⁺.

Example 9

N-{4-[2,4-Difluoro-3-(trifluoromethyl)phenyl]-1,3-thiazol-2-yl}-2-(5,7-dimethyl-4,6-dioxo-4,5,6,7-tetrahydro[1,2]thiazolo[3,4-d]pyrimidin-3-yl)acetamide

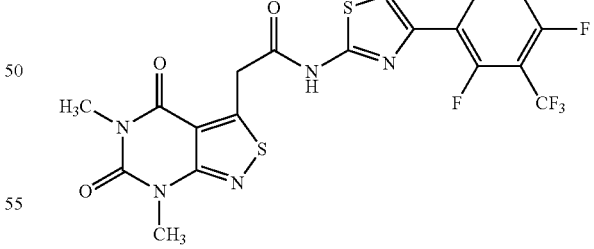

The title compound was prepared according to the general procedure (Method A) by coupling Intermediate 1 (500 mg, 1.960 mmol) with 4-[2,4-difluoro-3-(trifluoromethyl)phenyl]-1,3-thiazol-2-amine (548 mg, 1.960 mmol) in the presence of EDCI hydrochloride (451 mg, 2.352 mmol), HOBt (80 mg, 0.588 mmol) and DMAP (7 mg, 0.057 mmol) in 1,2-dichloroethane (19 ml) at reflux temperature to give 400 mg of the product as an pale yellow solid; $^1$H NMR (300 MHz, DMSO-$d_6$) δ 3.23 (s, 3H), 3.48 (s, 3H), 4.83 (s, 2H), 7.52 (t, J=8.1, 1H), 7.71 (s, 1H), 8.25-8.40 (m, 1H), 12.94 (br s, 1H); APCI-MS (m/z) 518.04 (M+H)+.

Example 10

N-{4-[3,5-Difluoro-4-(trifluoromethyl)phenyl]-1,3-thiazol-2-yl}-2-(5,7-dimethyl-4,6-dioxo-4,5,6,7-tetrahydro[1,2]thiazolo[3,4-d]pyrimidin-3-yl)acetamide

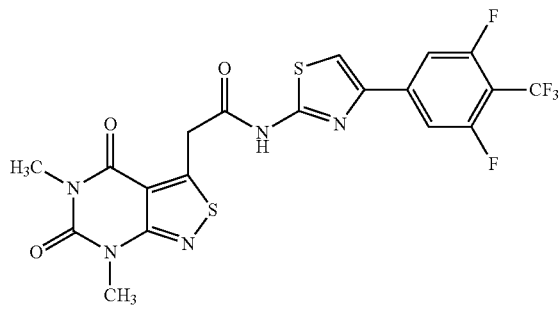 [SMILES: Cn1c(=O)c2c(CC(=O)Nc3nc(-c4cc(F)c(C(F)(F)F)c(F)c4)cs3)snc2n(C)c1=O]

The title compound was prepared according to the general procedure (Method A) by coupling Intermediate 1 (300 mg, 1.176 mmol) with 4-[3,5-difluoro-4-(trifluoromethyl)phenyl]-1,3-thiazol-2-amine (329 mg, 1.1776 mmol) in the presence of EDCI hydrochloride (270 mg, 1.411 mmol), HOBt (47 mg, 0.352 mmol) and DMAP (14.36 mg, 0.117 mmol) in 1,2-dichloroethane (11 ml) at reflux temperature to give 50 mg of the product off white solid; $^1$H NMR (300 MHz, DMSO-$d_6$) δ 3.16 (s, 3H), 3.48 (s, 3H), 4.84 (s, 2H), 7.85, 7.89 (2s, 2H), 8.16 (s, 1H), 12.98 (br s, 1H); APCI-MS (m/z) 518.13 (M+H)+.

Example 11

N-[1-(4-Bromophenyl)-1H-pyrazol-3-yl]-2-(5,7-dimethyl-4,6-dioxo-4,5,6,7-tetrahydro[1,2]thiazolo[3,4-d]pyrimidin-3-yl)acetamide

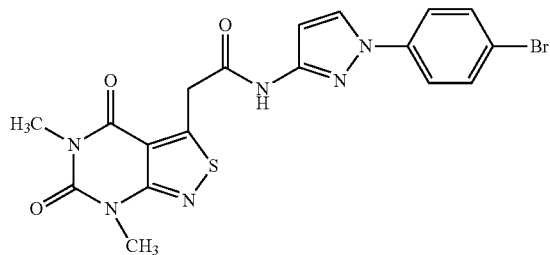 [SMILES: Cn1c(=O)c2c(CC(=O)Nc3ccn(-c4ccc(Br)cc4)n3)snc2n(C)c1=O]

The title compound was prepared according to the general procedure (Method A) by coupling Intermediate 1 (200 mg, 0.784 mmol) with 1-(4-bromophenyl)-1H-pyrazol-3-amine (186 mg, 0.784 mmol) in the presence of EDCI hydrochloride (180 mg, 0.940 mmol), HOBt (31 mg, 0.224 mmol) and DMAP (9.5 mg, 0.078 mmol) in 1,2-dichloroethane (7.8 ml) at reflux temperature to give 130 mg of the product as an pale yellow solid; $^1$H NMR (300 MHz, DMSO-$d_6$) δ 3.24 (s, 3H), 3.47 (s, 3H), 4.71 (s, 2H), 6.83 (s, 1H), 7.65-7.77 (m, 4H), 8.48 (s, 1H), 11.38 (br s, 1H); APCI-MS (m/z) 475.20 (M)+.

Example 12

N-[4-(4-Chlorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide

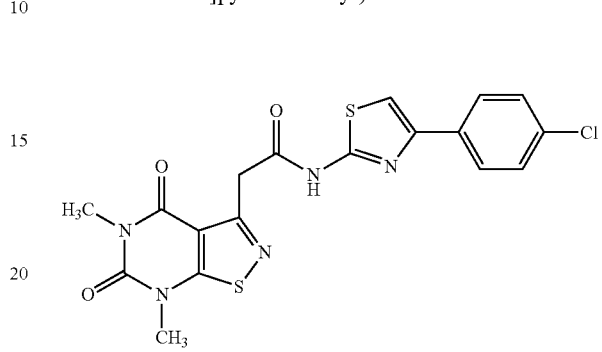

The title compound was prepared according to the general procedure (Method B) by coupling Intermediate 3 (200 mg, 0.706 mmol) with 4-(4-chlorophenyl)-1,3-thiazol-2-amine (178 mg, 0.847 mmol) in the presence of sodium hydride (60% dispersion in mineral oil, 56 mg, 1.412 mmol) in dry toluene (7 ml) to give 84 mg of the product as an off-white solid; $^1$H NMR (300 MHz, DMSO-$d_6$) δ 3.20 (s, 3H), 3.48 (s, 3H), 4.24 (s, 2H), 7.50 (d, J=8.4, 2H), 7.69 (s, 1H), 7.92 (d, J=8.1, 2H), 12.58 (br s, 1H); APCI-MS (m/z) 448.12 (M+H)+.

Example 13

2-(5,7-Dimethyl-4,6-dioxo-4,5,6,7-tetrahydro[1,2]thiazolo[5,4-d]pyrimidin-3-yl)-N-{4-[3-(trifluoromethyl)phenyl]-1,3-thiazol-2-yl}acetamide

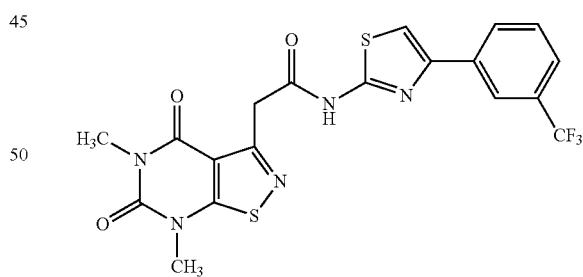

The title compound was prepared according to the general procedure (Method B) by coupling Intermediate 3 (200 mg, 0.706 mmol) with 4-[3-(trifluoromethyl)phenyl]-1,3-thiazol-2-amine (205 mg, 0.848 mmol) in the presence of sodium hydride (60% dispersion in mineral oil, 56 mg, 1.062 mmol) in dry toluene (5 ml) to give 23 mg of the product as an off-white solid; $^1$H NMR (300 MHz, CDCl$_3$) δ 3.49 (s, 3H), 3.58 (s, 3H), 4.35 (s, 2H), 7.21 (s, 1H), 7.47-7.57 (m, 2H), 7.99 (d, J=6.9, 1H), 8.11 (s, 1H), 10.57 (br s, 1H); APCI-MS (m/z) 482.13 (M+H)+.

Example 14

2-(5,7-Dimethyl-4,6-dioxo-4,5,6,7-tetrahydro[1,2]thiazolo[5,4-d]pyrimidin-3-yl)-N-{4-[4-(trifluoromethoxy)phenyl]-1,3-thiazol-2-yl}acetamide

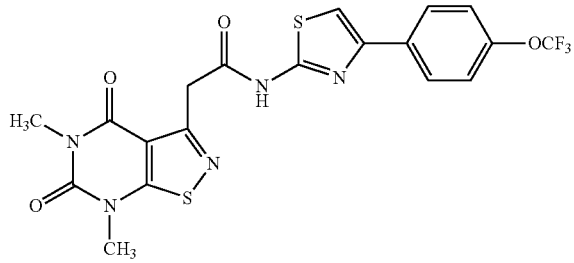

The title compound was prepared according to the general procedure (Method B) by coupling Intermediate 3 (90 mg, 0.318 mmol) with 4-[4-(trifluoromethoxy)phenyl]-1,3-thiazol-2-amine (99 mg, 0.381 mmol) in the presence of sodium hydride (60% dispersion in mineral oil, 25.2 mg, 0.630 mmol) in dry toluene (3 ml) to give 60 mg of the product as an off-white solid; $^1$H NMR (300 MHz, CDCl$_3$) δ 3.20 (s, 3H), 3.48 (s, 3H), 4.24 (s, 2H), 7.44 (d, J=8.1 Hz, 2H), 7.71 (s, 1H), 8.02 (d, J=8.7 Hz, 2H), 12.61 (br s, 1H); APCI-MS (m/z) 498.28 (M+H)$^+$.

Example 15

N-[4-(4-Bromophenyl)-1,3-thiazol-2-yl]-2-(5,7-dimethyl-4,6-dioxo-4,5,6,7-tetrahydro[1,2]thiazolo[3,4-d]pyrimidin-3-yl)acetamide

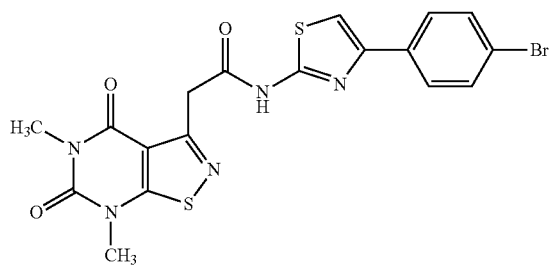 [SMILES: Cn1c(=O)c2c(CC(=O)Nc3nc(-c4ccc(Br)cc4)cs3)nsc2n(C)c1=O]

The title compound was prepared according to the general procedure (Method B) by coupling Intermediate 3 (150 mg, 0.530 mmol) with 4-[4-bromophenyl]-1,3-thiazol-2-amine (162 mg, 0.636 mmol) in the presence of in the presence in the presence of sodium hydride (60% dispersion in mineral oil, 42.4 mg, 1.06 mmol) in dry toluene (5.3 ml) to give 50 mg of the product as an off-white solid; $^1$H NMR (300 MHz, DMSO-d$_6$) δ 3.20 (s, 3H), 3.48 (s, 3H), 4.24 (s, 2H), 7.64 (d, J=8.4, 2H), 7.70 (s, 1H), 7.86 (d, J=8.4, 2H), 12.59 (br s, 1H); APCI-MS (m/z) 490.04 (M−H)$^−$.

Example 16

2-(5,7-Dimethyl-4,6-dioxo-4,5,6,7-tetrahydro[1,2]thiazolo[5,4-d]pyrimidin-3-yl)-N-[4-(4-tert butylphenyl)-1,3-thiazol-2-yl]acetamide

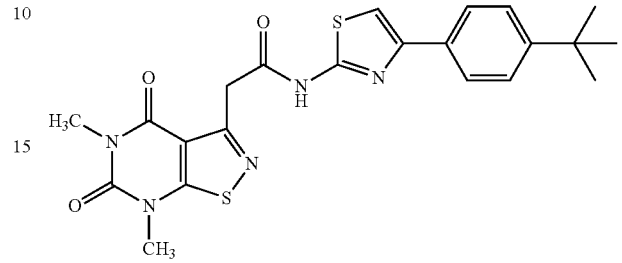

The title compound was prepared according to the general procedure (Method B) by coupling Intermediate 3 (150 mg, 0.530 mmol) with 4-[4-tert butylphenyl]-1,3-thiazol-2-amine (147 mg, 0.636 mmol) in the presence of in the presence in the presence of sodium hydride (60% dispersion in mineral oil, 42.4 mg, 1.06 mmol) in dry toluene (5.3 ml) to give 74 mg of the product as an off-white solid; $^1$H NMR (300 MHz, DMSO-d$_6$) δ 1.30 (s, 9H), 3.21 (s, 3H), 3.48 (s, 3H), 4.23 (s, 2H), 7.45 (d, J=8.1 Hz, 2H), 7.54 (s, 1H), 7.82 (d, J=8.4 Hz, 2H), 12.56 (br s, 1H); APCI-MS (m/z) 470.22 (M+H)$^+$.

Example 17

2-(5,7-Dimethyl-4,6-dioxo-4,5,6,7-tetrahydro[1,2]thiazolo[5,4-d]pyrimidin-3-yl)-N-[4-(4-ethyl phenyl)-1,3-thiazol-2-yl]acetamide

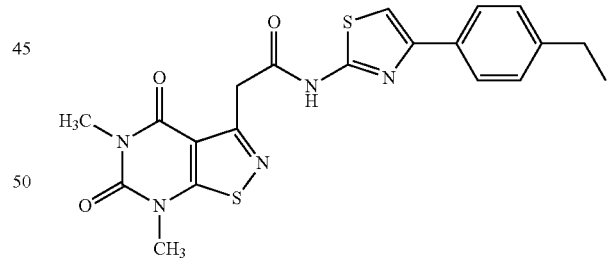

The title compound was prepared according to the general procedure (Method B) by coupling Intermediate 3 (150 mg, 0.530 mmol) with 4-[4-ethylphenyl]-1,3-thiazol-2-amine (147 mg, 0.636 mmol) in the presence of in the presence in the presence of sodium hydride (60% dispersion in mineral oil, 42.4 mg, 1.06 mmol) in dry toluene (5.3 ml) to give 120 mg of the product as an off-white solid; $^1$H NMR (300 MHz, DMSO-d$_6$) δ 1.20 (t, J=7.2, 3H), 2.62 (q, J=7.2, 2H), 3.21 (s, 3H), 3.48 (s, 3H), 4.19 (s, 2H), 7.25 (d, J=7.8, 2H), 7.43 (s, 1H), 7.80 (d, J=8.4, 2H), 12.59 (br s, 1H); APCI-MS (m/z) 442.22 (M+H)$^+$.

Example 18

2-(5,7-Dimethyl-4,6-dioxo-4,5,6,7-tetrahydro[1,2]
thiazolo[5,4-d]pyrimidin-3-yl)-N-[4-(4-cyclohexylphenyl)-1,3-thiazol-2-yl]acetamide

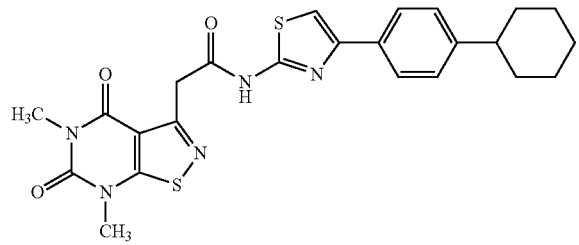 [SMILES: Cn1c(=O)c2c(CC(=O)Nc3nc(-c4ccc(C5CCCCC5)cc4)cs3)nsc2n(C)c1=O]

The title compound was prepared according to the general procedure (Method B) by coupling Intermediate 3 (150 mg, 0.530 mmol) with 4-[4-cyclohexylphenyl]-1,3-thiazol-2-amine (147 mg, 0.636 mmol) in the presence of in the presence in the presence of sodium hydride (60% dispersion in mineral oil, 42.4 mg, 1.06 mmol) in dry toluene (5.3 ml) to give 150 mg of the product as an off-white solid; $^1$H NMR (300 MHz, DMSO-$d_6$) δ 1.15-1.60 (m, 6H), 1.65-1.83 (m, 5H), 3.20 (s, 3H), 3.48 (s, 3H), 4.23 (s, 2H), 7.28 (d, J=8.4, 2H), 7.53 (s, 1H), 7.81 (d, J=7.8, 2H), 12.54 (br s, 1H); APCI-MS (m/z) 496.24 (M+H)$^+$.

Example 19

2-(5,7-Dimethyl-4,6-dioxo-4,5,6,7-tetrahydro[1,2]
thiazolo[5,4-d]pyrimidin-3-yl)-N-{4-[3-fluoro-4-(trifluoromethyl)phenyl]-1,3-thiazol-2-yl}acetamide

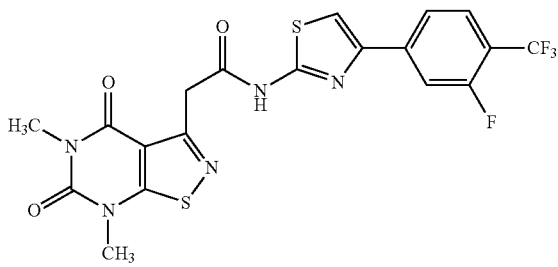

The title compound was prepared according to the general procedure (Method B) by coupling Intermediate 3 (200 mg, 0.706 mmol) with 4-(3-fluoro-4-(trifluoromethyl)phenyl)-1,3-thiazol-2-amine (222 mg, 0.848 mmol) in the presence of sodium hydride (60% dispersion in mineral oil, 56 mg, 1.413 mmol) in dry toluene (7 ml) to give 240 mg of the product as an off-white solid; $^1$H NMR (300 MHz, DMSO-$d_6$) δ 3.20 (s, 3H), 3.47 (s, 3H), 4.24 (s, 2H), 7.84-8.03 (m, 4H), 12.67 (br s, 1H); APCI-MS (m/z) 500.06 (M+H)$^+$.

Example 20

2-(5,7-Dimethyl-4,6-dioxo-4,5,6,7-tetrahydro[1,2]
thiazolo[5,4-d]pyrimidin-3-yl)-N-{4-[4-fluoro-3-(trifluoromethyl)phenyl]-1,3-thiazol-2-yl}acetamide

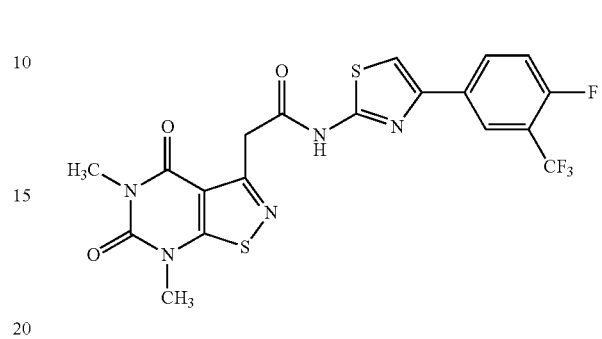

The title compound was prepared according to the general procedure (Method A) by coupling Intermediate 2 (175 mg, 0.686 mmol) with 4-(4-fluoro-3-(trifluoromethyl)phenyl)-1,3-thiazol-2-amine (179 mg, 0.686 mmol) in the presence of EDCI hydrochloride (133 mg, 0.823 mmol), HOBt (27 mg, 0.205 mmol) and DMAP (8.38 mg, 0.068 mmol) in 1,2-dichloroethane (7 ml) at reflux temperature to give 16 mg of the product as an off-white solid; $^1$H NMR (300 MHz, DMSO-$d_6$) δ 3.20 (s, 3H), 3.47 (s, 3H), 4.23 (s, 2H), 7.62 (t, J=9.0 Hz, 1H), 7.86 (s, 1H), 8.23-8.31 (m, 2H), 12.64 (br s, 1H); APCI-MS (m/z) 500.09 (M+H)$^+$.

Example 21

2-(5,7-Dimethyl-4,6-dioxo-4,5,6,7-tetrahydro[1,2]
thiazolo[5,4-d]pyrimidin-3-yl)-N-{4-[2-fluoro-4-(trifluoromethyl)phenyl]-1,3-thiazol-2-yl}acetamide

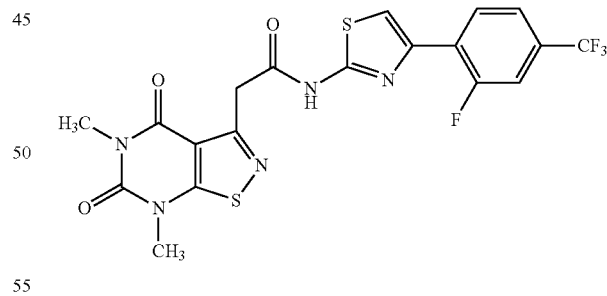

The title compound was prepared according to the general procedure (Method B) by coupling Intermediate 3 (150 mg, 0.530 mmol) with 4-(2-fluoro-4-(trifluoromethyl)phenyl)-1,3-thiazol-2-amine (166 mg, 0.836 mmol) in the presence of sodium hydride (60% dispersion in mineral oil, 42.3 mg, 1.060 mmol) in dry toluene (6 ml) to give 80 mg of the product as an off-white solid; $^1$H NMR (300 MHz, DMSO-$d_6$) δ 3.20 (s, 3H), 3.48 (s, 3H), 4.25 (s, 2H), 7.69-7.78 (m, 2H), 7.82 (d, J=11.7 Hz, 1H), 8.26 (t, J=8.1 Hz, 1H), 12.68 (br s, 1H); APCI-MS (m/z) 500.01 (M+H)$^+$.

Example 22

2-(5,7-Dimethyl-4,6-dioxo-4,5,6,7-tetrahydro[1,2]
thiazolo[5,4-d]pyrimidin-3-yl)-N-{4-[3-fluoro-5-
(trifluoromethyl)phenyl]-1,3-thiazol-2-yl}acetamide

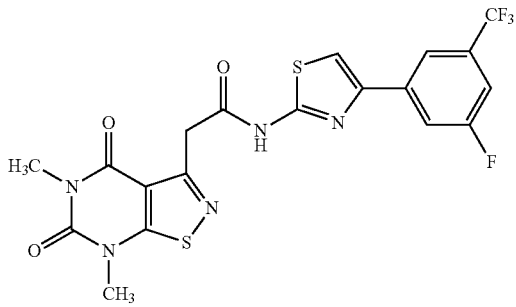 [SMILES: Cn1c(=O)c2c(CC(=O)Nc3nc(-c4cc(F)cc(C(F)(F)F)c4)cs3)nsc2n(C)c1=O]

The title compound was prepared according to the general procedure (Method B) by coupling Intermediate 3 (200 mg, 0.706 mmol) with 4-(3-fluoro-5-(trifluoromethyl)phenyl)-1,3-thiazol-2-amine (221 mg, 0.847 mmol) in the presence of sodium hydride (60% dispersion in mineral oil, 56.0 mg, 1.41 mmol) in dry toluene (6 ml) to give 50 mg of the product as an off-white solid; $^1$H NMR (300 MHz, DMSO-$d_6$) δ 3.20 (s, 3H), 3.48 (s, 3H), 4.24 (s, 2H), 7.66 (d, J=8.1.7 Hz, 1H), 8.00-8.14 (m, 3H), 12.67 (br s, 1H); APCI-MS (m/z) 500.22 (M+H)$^+$.

Example 23

2-(5,7-Dimethyl-4,6-dioxo-4,5,6,7-tetrahydro[1,2]
thiazolo[5,4-d]pyrimidin-3-yl)-N-{4-[2-fluoro-3-
(trifluoromethyl)phenyl]-1,3-thiazol-2-yl}acetamide

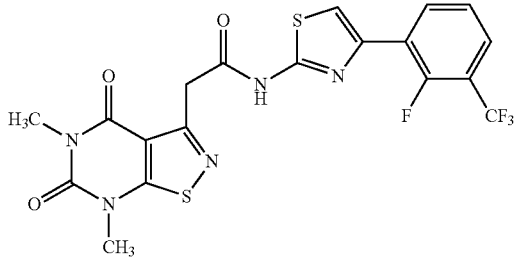

The title compound was prepared according to the general procedure (Method B) by coupling Intermediate 3 (150 mg, 0.530 mmol) with 4-[2-fluoro-3-(trifluoromethyl)phenyl]-1,3-thiazol-2-amine (166 mg, 0.636 mmol) in the presence of sodium hydride (60% dispersion in mineral oil, 42.3 mg, 1.060 mmol) in dry toluene (6 ml) to give 130 mg of the product as an off-white solid; $^1$H NMR (300 MHz, DMSO-$d_6$) δ 3.20 (s, 3H), 3.48 (s, 3H), 4.25 (s, 2H), 7.54 (t, J=7.8 Hz, 1H), 7.68 (s, 1H), 7.78 (t, J=6.9 Hz, 1H), 8.33 (t, J=7.5 Hz, 1H), 12.67 (br s, 1H); APCI-MS (m/z) 500.09 (M+H)$^+$.

Example 24

2-(5,7-Dimethyl-4,6-dioxo-4,5,6,7-tetrahydro[1,2]
thiazolo[5,4-d]pyrimidin-3-yl)-N-{4-[4-fluoro-3-
(trifluoromethoxy)phenyl]-1,3-thiazol-2-
yl}acetamide

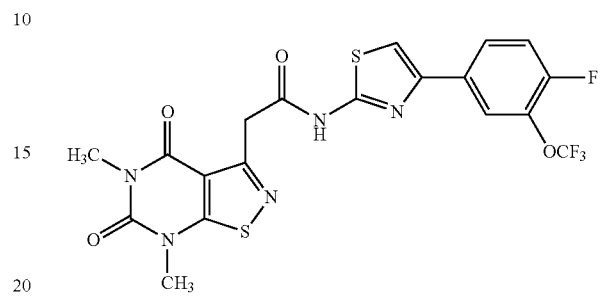

The title compound was prepared according to the general procedure (Method B) by coupling Intermediate 3 (200 mg, 0.706 mmol) with 4-(4-fluoro-3-(trifluoromethoxy)phenyl)-1,3-thiazol-2-amine (235 mg, 0.848 mmol) in the presence of sodium hydride (60% dispersion in mineral oil, 56.5 mg, 1.413 mmol) in dry toluene (7 ml) to give 105 mg of the product as an off-white solid; $^1$H NMR (300 MHz, DMSO-$d_6$) δ 3.20 (s, 3H), 3.47 (s, 3H), 4.23 (s, 2H), 7.60 (t, J=9.0 Hz, 1H), 7.80 (s, 1H), 7.96-8.06 (m, 2H), 12.62 (br s, 1H); APCI-MS (m/z) 516.09 (M+H)$^+$.

Example 25

2-(5,7-Dimethyl-4,6-dioxo-4,5,6,7-tetrahydro[1,2]
thiazolo[5,4-d]pyrimidin-3-yl)-N-{4-[3-fluoro-4-
(trifluoromethoxy)phenyl]-1,3-thiazol-2-
yl}acetamide

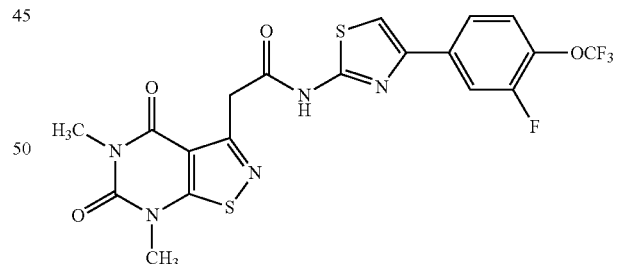

The title compound was prepared according to the general procedure (Method B) by coupling Intermediate 3 (200 mg, 0.706 mmol) with 4-(3-fluoro-4-(trifluoromethoxy)phenyl)-1,3-thiazol-2-amine (235 mg, 0.848 mmol) in the presence of sodium hydride (60% dispersion in mineral oil, 56.5 mg, 1.413 mmol) in dry toluene (7 ml) to give 140 mg of the product as an off-white solid; $^1$H NMR (300 MHz, DMSO-$d_6$) δ 3.20 (s, 3H), 3.48 (s, 3H), 4.24 (s, 2H), 7.66 (t, J=8.1 Hz, 1H), 7.83-7.89 (m, 2H), 7.98 (d, J=11.7, 2H), 12.64 (br s, 1H); APCI-MS (m/z) 516.03 (M+H)$^+$.

Example 26

N-[4-(3,4-Dichlorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide

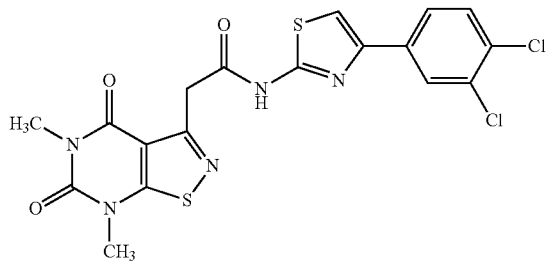

The title compound was prepared according to the general procedure (Method B) by coupling Intermediate 3 (200 mg, 0.706 mmol) with 4-(3,4-dichlorophenyl)-1,3-thiazol-2-amine (207 mg, 0.848 mmol) in the presence of sodium hydride (60% dispersion in mineral oil, 56.5 mg, 1.413 mmol) in dry toluene (7 ml) to give 110 mg of the product as an off-white solid; $^1$H NMR (300 MHz, DMSO-$d_6$) δ 3.20 (s, 3H), 3.47 (s, 3H), 4.24 (s, 2H), 7.71 (d, J=8.4 Hz, 1H), 7.84 (s, 1H), 7.89 (d, J=8.4, 1H), 8.15 (s, 1H), 12.61 (br s, 1H); APCI-MS (m/z) 482.16 (M)$^+$.

Example 27

N-[4-(3,4-Difluorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide

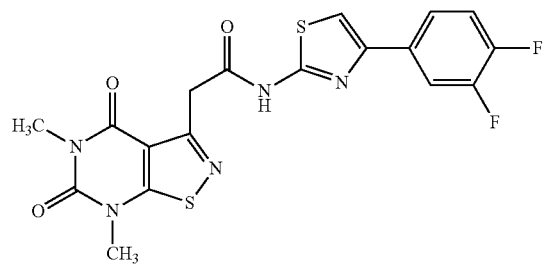

The title compound was prepared according to the general procedure (Method B) by coupling Intermediate 3 (200 mg, 0.706 mmol) with 4-(3,4-difluorophenyl)-1,3-thiazol-2-amine (179 mg, 0.848 mmol) in the presence of sodium hydride (60% dispersion in mineral oil, 56.5 mg, 1.413 mmol) in dry toluene (7 ml) to give 60 mg of the product as an off-white solid; $^1$H NMR (300 MHz, DMSO-$d_6$) δ 3.20 (s, 3H), 3.48 (s, 3H), 4.24 (s, 2H), 7.52 (q, J=8.4 Hz, 1H), 7.59-7.87 (m, 2H), 7.88-7.97 (m, 1H), 12.59 (br s, 1H); APCI-MS (m/z) 450.06 (M+H)$^+$.

Example 28

N-[4-(2,4-Difluorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide

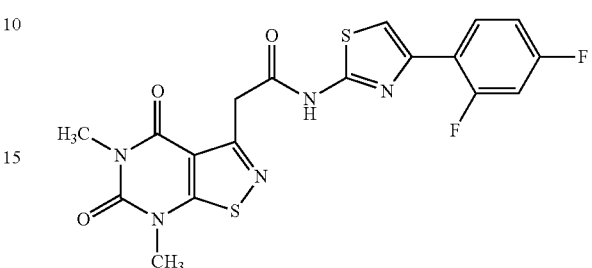

The title compound was prepared according to the general procedure (Method B) by coupling Intermediate 3 (200 mg, 0.706 mmol) with 4-(2,4-difluorophenyl)-1,3-thiazol-2-amine (179 mg, 0.848 mmol) in the presence of sodium hydride (60% dispersion in mineral oil, 56.5 mg, 1.413 mmol) in dry toluene (7 ml) to give 180 mg of the product as an off-white solid; $^1$H NMR (300 MHz, DMSO-$d_6$) δ 3.21 (s, 3H), 3.48 (s, 3H), 4.12 (s, 2H), 7.11-7.36 (m, 3H), 8.06 (q, J=8.7, 1H), 12.62 (br s, 1H); APCI-MS (m/z) 450.06 (M+H)$^+$.

Example 29

2-(5,7-Dimethyl-4,6-dioxo-4,5,6,7-tetrahydro[1,2]thiazolo[5,4-d]pyrimidin-3-yl)-N-{4-[4-chloro-3-(trifluoromethyl)phenyl]-1,3-thiazol-2-yl}acetamide

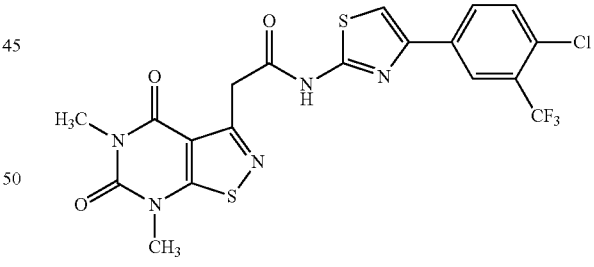

The title compound was prepared according to the general procedure (Method B) by coupling Intermediate 3 (200 mg, 0.706 mmol) with 4-[4-chloro-3-(trifluoromethyl)phenyl]-1,3-thiazol-2-amine (236 mg, 0.848 mmol) in the presence of sodium hydride (60% dispersion in mineral oil, 56.5 mg, 1.413 mmol) in dry toluene (7 ml) to give 160 mg of the product as an off-white solid; $^1$H NMR (300 MHz, DMSO-$d_6$) δ 3.20 (s, 3H), 3.47 (s, 3H), 4.24 (s, 2H), 7.81 (d, J=8.4 Hz, 1H), 7.94 (s, 1H), 8.21 (d, J=8.4 Hz, 1H), 8.35 (s, 1H), 12.67 (br s, 1H); APCI-MS (m/z) 516.22 (M+H)$^+$.

Example 30

2-(5,7-Dimethyl-4,6-dioxo-4,5,6,7-tetrahydro[1,2]thiazolo[5,4-d]pyrimidin-3-yl)-N-{4-[3-chloro-4-(trifluoromethoxy)phenyl]-1,3-thiazol-2-yl}acetamide

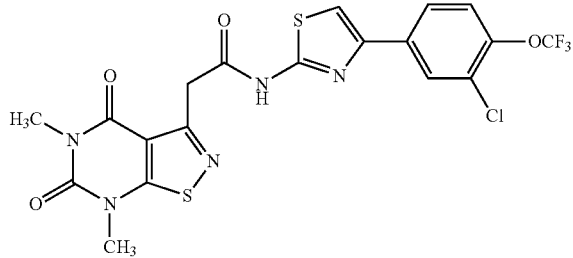 [SMILES: Cn1c(=O)c2c(CC(=O)Nc3nc(-c4ccc(OC(F)(F)F)c(F)c4)cs3)nsc2n(C)c1=O]

The title compound was prepared according to the general procedure (Method B) by coupling Intermediate 3 (200 mg, 0.706 mmol) with 4-(3-chloro-4-(trifluoromethoxy)phenyl)-1,3-thiazol-2-amine (249 mg, 0.848 mmol) in the presence of sodium hydride (60% dispersion in mineral oil, 56.5 mg, 1.413 mmol) in dry toluene (7 ml) to give 55 mg of the product as an off-white solid; $^1$H NMR (300 MHz, DMSO-$d_6$) δ 3.18 (s, 3H), 3.46 (s, 3H), 4.22 (s, 2H), 7.64 (d, J=8.1 Hz, 1H), 7.85 (s, 1H), 7.97 (d, J=9.3 Hz, 1H), 8.17 (s, 1H), 12.62 (br s, 1H); APCI-MS (m/z) 532.11 (M+H)$^+$.

Example 31

2-(5,7-Dimethyl-4,6-dioxo-4,5,6,7-tetrahydro[1,2]thiazolo[5,4-d]pyrimidin-3-yl)-N-{4-[4-chloro-3-(trifluoromethoxy)phenyl]-1,3-thiazol-2-yl}acetamide

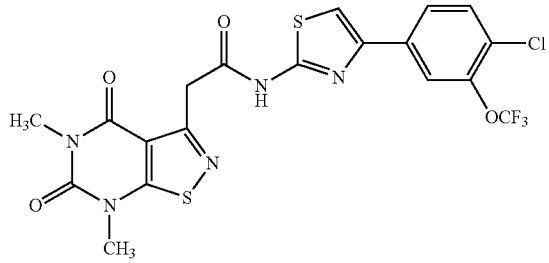 [SMILES: Cn1c(=O)c2c(CC(=O)Nc3nc(-c4ccc(Cl)c(OC(F)(F)F)c4)cs3)nsc2n(C)c1=O]

The title compound was prepared according to the general procedure (Method B) by coupling Intermediate 3 (150 mg, 0.530 mmol) with 4-(4-chloro-3-(trifluoromethoxy)phenyl)-1,3-thiazol-2-amine (187 mg, 0.636 mmol) in the presence of sodium hydride (60% dispersion in mineral oil, 42.5 mg, 1.06 mmol) in dry toluene (5.6 ml) to give 110 mg of the product as an off-white solid; $^1$H NMR (300 MHz, DMSO-$d_6$) δ 3.20 (s, 3H), 3.48 (s, 3H), 4.23 (s, 2H), 7.77 (t, J=8.4 Hz, 1H), 7.86 (s, 1H), 7.97-8.05 (m, 2H), 12.63 (br s, 1H); APCI-MS (m/z) 532.15 (M+H)$^+$.

Example 32

2-(5,7-Dimethyl-4,6-dioxo-4,5,6,7-tetrahydro[1,2]thiazolo[5,4-d]pyrimidin-3-yl)-N-{4-[3-chloro-5-(trifluoromethyl)phenyl]-1,3-thiazol-2-yl}acetamide

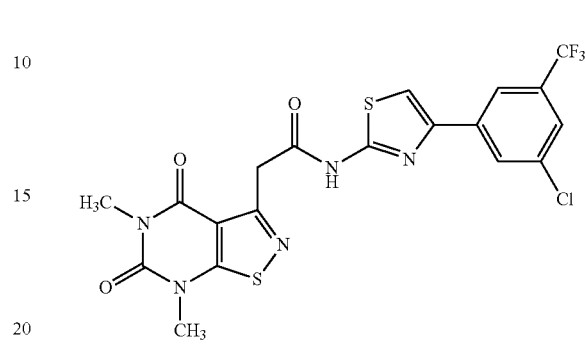

The title compound was prepared according to the general procedure (Method B) by coupling Intermediate 3 (150 mg, 0.530 mmol) with 4-(3-chloro-5-(trifluoromethyl)phenyl)-1,3-thiazol-2-amine (177 mg, 0.636 mmol) in the presence of sodium hydride (60% dispersion in mineral oil, 42.0 mg, 1.06 mmol) in dry toluene (5.3 ml) to give 123 mg of the product as an off-white solid; $^1$H NMR (300 MHz, DMSO-$d_6$) δ 3.20 (s, 3H), 3.48 (s, 3H), 4.24 (s, 2H), 7.83 (s, 1H), 8.05 (s, 1H), 8.23 (s, 1H), 8.30 (s, 1H), 12.67 (br s, 1H); APCI-MS (m/z) 516.05 (M+H)$^+$.

Example 33

2-(5,7-Dimethyl-4,6-dioxo-4,5,6,7-tetrahydro[1,2]thiazolo[5,4-d]pyrimidin-3-yl)-N-{4-[2-fluoro-5-(trifluoromethyl)phenyl]-1,3-thiazol-2-yl}acetamide

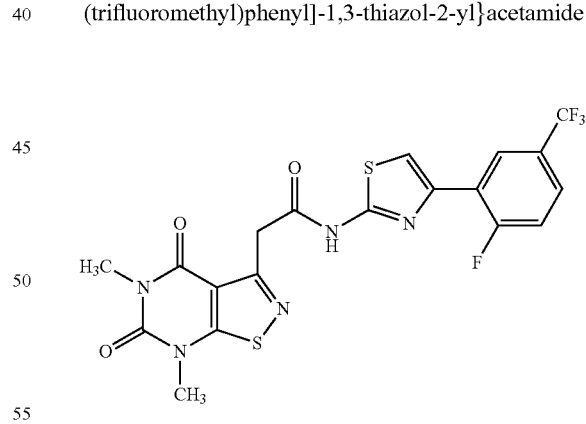

The title compound was prepared according to the general procedure (Method B) by coupling Intermediate 3 (150 mg, 0.530 mmol) with 4-(2-fluoro-5-(trifluoromethyl)phenyl)-1,3-thiazol-2-amine (166 mg, 0.636 mmol) in the presence of sodium hydride (60% dispersion in mineral oil, 42 mg, 1.06 mmol) in dry toluene (5.3 ml) to give 90 mg of the product as an off-white solid; $^1$H NMR (300 MHz, DMSO-$d_6$) δ 3.21 (s, 3H), 3.48 (s, 3H), 4.24 (s, 2H), 7.60 (t, J=8.7, 1H), 7.69 (s, 1H), 7.78 (s, 1H), 8.41 (d, J=6.3, 1H), 12.69 (br s, 1H); APCI-MS (m/z) 500.06 (M+H)$^+$.

Example 34

N-[4-(3,5-Dichlorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide

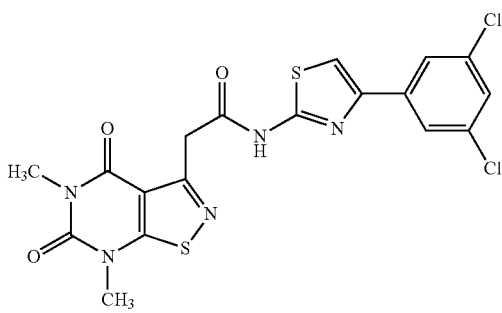 [SMILES: Cn1c(=O)c2c(CC(=O)Nc3nc(-c4cc(Cl)cc(Cl)c4)cs3)nsc2n(C)c1=O]

The title compound was prepared according to the general procedure (Method B) by coupling Intermediate 3 (150 mg, 0.530 mmol) with 4-(3,5-dichlorophenyl)-1,3-thiazol-2-amine (155 mg, 0.636 mmol) in the presence of sodium hydride (60% dispersion in mineral oil, 42.5 mg, 1.06 mmol) in dry toluene (5.3 ml) to give 17 mg of the product as an off-white solid; $^1$H NMR (300 MHz, DMSO-$d_6$) δ 3.20 (s, 3H), 3.48 (s, 3H), 4.24 (s, 2H), 7.57 (s, 1H), 7.92-7.97 (m, 3H), 12.62 (br s, 1H); APCI-MS (m/z) 480.13 (M−H)$^-$.

Example 35

N-{4-[4-(Difluoromethoxy)-3-fluorophenyl]-1,3-thiazol-2-yl}-2-(5,7-dimethyl-4,6-dioxo-4,5,6,7-tetrahydro[1,2]thiazolo[5,4-d]pyrimidin-3-yl)acetamide

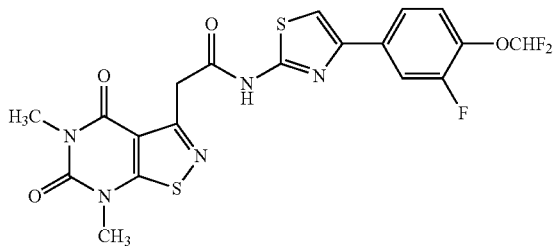 [SMILES: Cn1c(=O)c2c(CC(=O)Nc3nc(-c4ccc(OC(F)F)c(F)c4)cs3)nsc2n(C)c1=O]

The title compound was prepared according to the general procedure (Method B) by coupling Intermediate 3 (100 mg, 0.353 mmol) with 4-[4-(difluoromethoxy)-3-fluorophenyl]-1,3-thiazol-2-amine (110 mg, 0.423 mmol) in the presence of sodium hydride (60% dispersion in mineral oil, 26 mg, 0.530 mmol) in dry toluene (5.3 ml) to give 70 mg of the product as an off-white solid; $^1$H NMR (300 MHz, DMSO-$d_6$) δ 3.20 (s, 3H), 3.48 (s, 3H), 4.24 (s, 2H), 7.29 (t, J=72.9 Hz, 1H), 7.45 (t, J=8.4 Hz, 1H), 7.73-7.93 (m, 3H), 12.60 (br s, 1H); APCI-MS (m/z) 498.23 (M+H)$^+$.

Example 36

N-{4-[3-Chloro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide

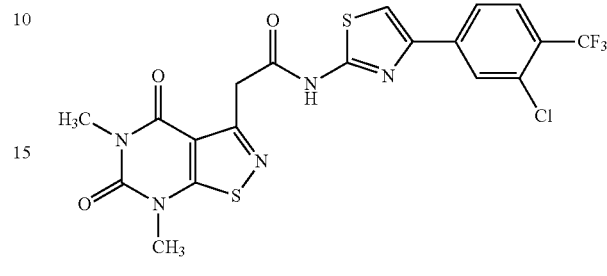

The title compound was prepared according to the general procedure (Method B) by coupling Intermediate 3 (85 mg, 0.300 mmol) with 4-[3-chloro-4-(trifluoromethyl)phenyl]-1,3-thiazol-2-amine (100 mg, 0.360 mmol) in the presence of sodium hydride (60% dispersion in mineral oil, 24 mg, 0.600 mmol) in dry toluene (3 ml) to give 32 mg of the product as an off-white solid; $^1$H NMR (300 MHz, DMSO-$d_6$) δ 3.21 (s, 3H), 3.48 (s, 3H), 4.19 (s, 2H), 7.89-7.93 (m, 2H), 8.04 (d, J=8.1 Hz, 1H), 8.20 (s, 1H), 12.59 (br s, 1H); APCI-MS (m/z) 516.12 (M+H)$^+$.

Example 37

N-{4-[2,4-Difluoro-3-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide

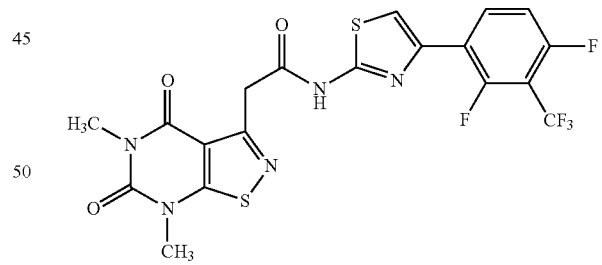

The title compound was prepared according to the general procedure (Method A) by coupling Intermediate 2 (175 mg, 0.686 mmol) with 4-[2,4-difluoro-3-(trifluoromethyl)phenyl]-1,3-thiazol-2-amine (192 mg, 0.686 mmol) in the presence of EDCI hydrochloride (160 mg, 0.834 mmol), HOBt (28 mg, 0.207 mmol) and DMAP (9 mg, 0.068 mmol) in 1,2-dichloroethane (8.3 ml) at room temperature to give 22 mg of the product as an off-white solid; $^1$H NMR (300 MHz, DMSO-$d_6$) δ 3.20 (s, 3H), 3.48 (s, 3H), 4.25 (s, 2H), 7.52 (t, J=9.3 Hz, 1H), 7.64 (s, 1H), 8.29-8.37 (m, 1H), 12.65 (br s, 1H); APCI-MS (m/z) 516.07 (M−H)$^-$.

Example 38

N-{4-[3,5-difluoro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide

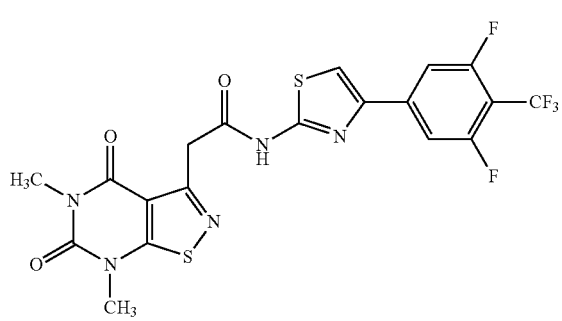 [SMILES: Cn1c(=O)c2c(CC(=O)Nc3nc(-c4cc(F)c(C(F)(F)F)c(F)c4)cs3)nsc2n(C)c1=O]

The title compound was prepared according to the general procedure (Method A) by coupling Intermediate 2 (200 mg, 0.784 mmol) with 4-[3,5-difluoro-4-(trifluoromethyl)phenyl]-1,3-thiazol-2-amine (220 mg, 0.784 mmol) in the presence of EDCI hydrochloride (180 mg, 0.941 mmol), HOBt (32 mg, 0.235 mmol) and DMAP (9.5 mg, 0.078 mmol) in 1,2-dichloroethane (8 ml) at reflux temperature to give 33 mg of the product as an off-white solid; $^1$H NMR (300 MHz, DMSO-$d_6$) δ 3.20 (s, 3H), 3.47 (s, 3H), 4.24 (s, 2H), 7.83 (s, 1H), 7.87 (s, 1H), 8.09 (s, 1H), 12.69 (br s, 1H); APCI-MS (m/z) 518.01 (M+H)$^+$.

Example 39

N-{4-[2,3-Difluoro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide

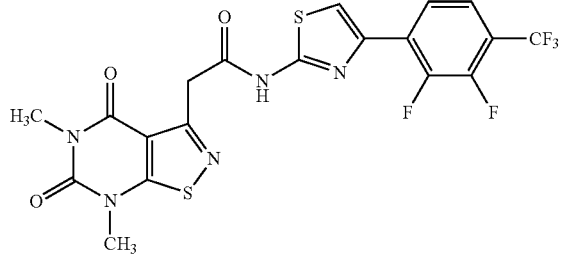 [SMILES: Cn1c(=O)c2c(CC(=O)Nc3nc(-c4ccc(C(F)(F)F)c(F)c4F)cs3)nsc2n(C)c1=O]

The title compound was prepared according to the general procedure (Method B) by coupling Intermediate 3 (50 mg, 0.176 mmol) with 4-[2,3-difluoro-4-(trifluoromethyl)phenyl]-1,3-thiazol-2-amine (59 mg, 0.212 mmol) in the presence of sodium hydride (60% dispersion in mineral oil, 14.5 mg, 0.352 mmol) in dry toluene (3 ml) to give 50 mg of the product as an off-white solid; $^1$H NMR (300 MHz, DMSO-$d_6$) δ 3.20 (s, 3H), 3.48 (s, 3H), 4.25 (s, 2H), 7.78 (t, J=7.2 Hz, 1H), 7.82 (s, 1H), 8.02 (t, J=7.5 Hz, 1H), 12.73 (br s, 1H); APCI-MS (m/z) 518.10 (M+H)$^+$.

Example 40

N-{4-[4-(Difluoromethoxy)-3,5-difluorophenyl]-1,3-thiazol-2-yl}-2-(5,7-dimethyl-4,6-dioxo-4,5,6,7-tetrahydroisothiazolo[3,4-d]pyrimidin-3-yl)acetamide

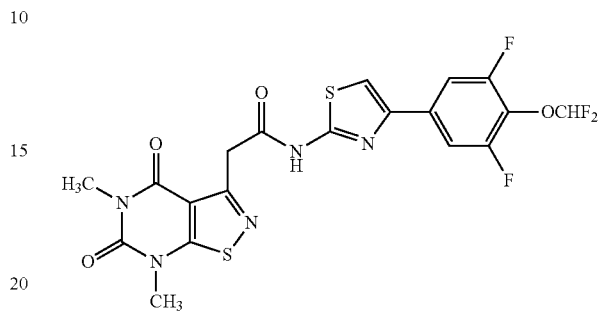

The title compound was prepared according to the general procedure (Method A) by coupling Intermediate 2 (200 mg, 0.784 mmol) with 4-[4-(difluoromethoxy)-3,5-difluorophenyl]-1,3-thiazol-2-amine (216 mg, 0.784 mmol) in the presence of EDCI hydrochloride (180 mg, 0.941 mmol), HOBt (32 mg, 0.235 mmol) and DMAP (9.5 mg, 0.078 mmol) in 1,2-dichloroethane (8 ml) at reflux temperature to give 38 mg of the product as an off-white solid; $^1$H NMR (300 MHz, DMSO-$d_6$) δ 3.18 (s, 3H), 3.45 (s, 3H), 4.22 (s, 2H), 7.26 (t, J=72.3 Hz, 1H), 7.76 (s, 1H), 7.79 (s, 1H), 7.87 (s, 1H), 12.62 (br s, 1H); APCI-MS (m/z) 516.05 (M+H)$^+$.

Example 41

N-[4-(2,4-Dichloro-5-fluorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide

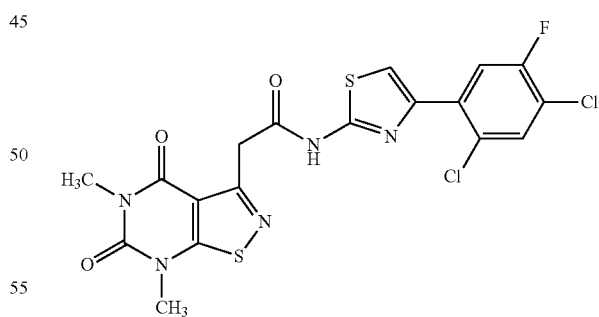

The title compound was prepared according to the general procedure (Method B) by coupling Intermediate 3 (89 mg, 0.314 mmol) with 4-(2,4-dichloro-5-fluorophenyl)-1,3-thiazol-2-amine (100 mg, 0.377 mmol) in the presence of sodium hydride (60% dispersion in mineral oil, 25 mg, 0.628 mmol) in dry toluene (3 ml) to give 41 mg of the product as an off-white solid; $^1$H NMR (300 MHz, DMSO-$d_6$) δ 3.21 (s, 3H), 3.48 (s, 3H), 4.23 (s, 2H), 7.76 (s, 1H), 7.85-7.95 (m, 2H), 12.63 (br s, 1H); APCI-MS (m/z) 499.99 (M)$^+$.

Example 42

N-[5-(4-bromophenyl)-1,3,4-thiadiazol-2-yl]-2-(5,7-dimethyl-4,6-dioxo-4,5,6,7-tetrahydro[1,2]thiazolo[5,4-d]pyrimidin-3-yl)acetamide

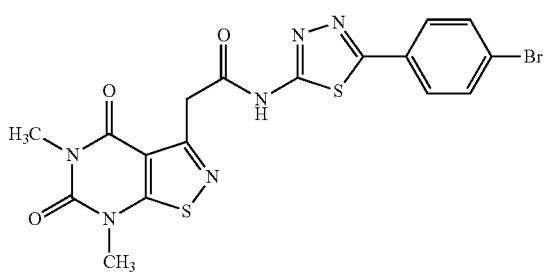 [SMILES: Cn1c(=O)c2c(CC(=O)Nc3nnc(-c4ccc(Br)cc4)s3)nsc2n(C)c1=O]

The title compound was prepared according to the general procedure (Method B) by coupling Intermediate 3 (150 mg, 0.530 mmol) with 5-(4-bromophenyl)-1,3,4-thiadiazol-2-amine (162 mg, 0.636 mmol) in the presence of sodium hydride (60% dispersion in mineral oil, 42.4 mg, 1.06 mmol) in dry toluene (5.3 ml) to give 240 mg of the product as an off-white solid; $^1$H NMR (300 MHz, DMSO-$d_6$) δ 3.20 (s, 3H), 3.47 (s, 3H), 4.28 (s, 2H), 7.73 (t, J=8.1 Hz, 1H), 7.87 (d, J=8.7 Hz, 1H), 12.73 (br s, 1H); APCI-MS (m/z) 493.23 (M)$^+$.

Example 43

N-[3-(4-Chlorophenyl)-1H-pyrazol-5-yl]-2-(5,7-dimethyl-4,6-dioxo-4,5,6,7-tetrahydro[1,2]thiazolo[5,4-d]pyrimidin-3-yl)acetamide

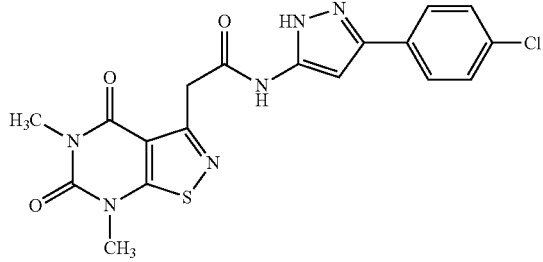 [SMILES: Cn1c(=O)c2c(CC(=O)Nc3cc(-c4ccc(Cl)cc4)n[nH]3)nsc2n(C)c1=O]

The title compound was prepared according to the general procedure (Method B) by coupling Intermediate 3 (150 mg, 0.530 mmol) with 3-(4-chlorophenyl)-1H-pyrazol-5-amine (123 mg, 0.636 mmol) in the presence in the presence of sodium hydride (60% dispersion in mineral oil, 31.8 mg, 0.79 mmol) in dry toluene (5.3 ml) to give 60 mg of the product as an off-white solid; $^1$H NMR (300 MHz, DMSO-$d_6$) δ 3.16 (s, 3H), 3.47 (s, 3H), 4.11 (s, 2H), 6.82 (s, 1H), 7.49 (d, J=8.1, 2H), 7.72 (d, J=8.7, 2H), 10.75 (s, 1H), 12.92 (br s, 1H); APCI-MS (m/z) 431.08 (M)$^+$.

Example 44

N-[1-(4-Bromophenyl)-1H-pyrazol-3-yl]-2-(5,7-dimethyl-4,6-dioxo-4,5,6,7-tetrahydro[1,2]thiazolo[5,4-d]pyrimidin-3-yl)acetamide

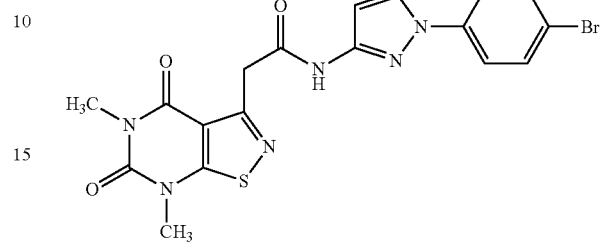

The title compound was prepared according to the general procedure (Method B) by coupling Intermediate 3 (150 mg, 0.530 mmol) with 1-(4-bromophenyl)-1H-pyrazol-3-amine (151 mg, 0.636 mmol) in the presence in the presence of sodium hydride (60% dispersion in mineral oil, 42.4 mg, 1.06 mmol) in dry toluene (5.3 ml) to give 80 mg of the product as an off-white solid; $^1$H NMR (300 MHz, DMSO-$d_6$) δ 3.20 (s, 3H), 3.47 (s, 3H), 4.13 (s, 2H), 6.73 (s, 1H), 7.68 (d, J=9.0, 2H), 7.74 (d, J=9.0, 2H), 8.42 (s, 1H), 11.01 (br s, 1H); APCI-MS (m/z) 475.11 (M)$^+$.

Example 45

N-[3-(4-Chlorophenyl)-1,2-oxazol-5-yl]-2-(5,7-dimethyl-4,6-dioxo-4,5,6,7-tetrahydro[1,2]thiazolo[5,4-d]pyrimidin-3-yl)acetamide

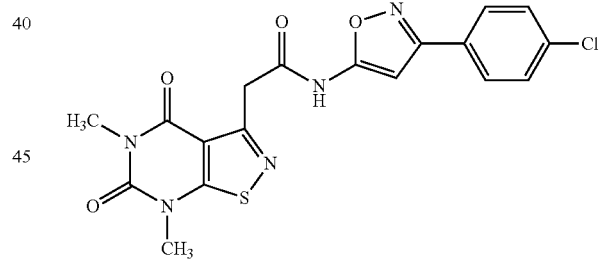

The title compound was prepared according to the general procedure (Method B) by coupling Intermediate 3 (150 mg, 0.530 mmol) with 3-(4-chlorophenyl)isoxazol-5-amine (123 mg, 0.636 mmol) in the presence in the presence of sodium hydride (60% dispersion in mineral oil, 42.4 mg, 1.06 mmol) in dry toluene (5.3 ml) to give 80 mg of the product as an off-white solid; $^1$H NMR (300 MHz, DMSO-$d_6$) δ 3.21 (s, 3H), 3.48 (s, 3H), 4.19 (s, 2H), 6.69 (s, 1H), 7.56 (d, J=8.4, 2H), 7.87 (d, J=8.7, 2H), 12.10 (br s, 1H); APCI-MS (m/z) 432.30 (M+H)$^+$.

Using the similar procedure as described in method A or B, additional examples of isothiazolopyrimidinedione acetamides with multiple fluorine substitutions (as depicted in Table 3) can be prepared by coupling isothiazolo[5,4-d]pyrimidinedione acetic acid or isothiazolo[3,4-d]pyrimidinedione acetic acid or their ester with an appropriate fluorinated 2-amino-4-arylthiazole selected from Table 2.

TABLE 3

Additional examples of fluorinated furopyrimindiedione acetamide derivatives

| S No. | Molecular structure | Chemical name | Mol. Formula | Mol Wt. |
|---|---|---|---|---|
| 1 | 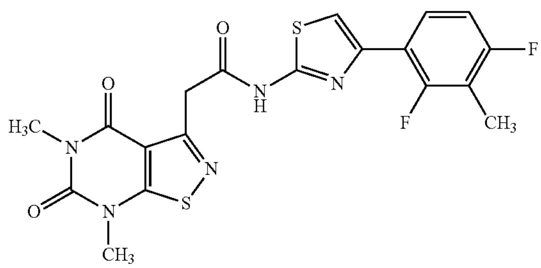 | 2-(5,7-Dimethyl-4,6-dioxo-4,5,6,7-tetrahydro[1,2]thiazolo[5,4-d]pyrimidin-3-yl)-N-{4-[2,4-difluoro-3-methylphenyl]-1,3-thiazol-2-yl}acetamide | $C_{19}H_{15}F_2N_5O_3S_2$ | 463.49 |
| 2 | 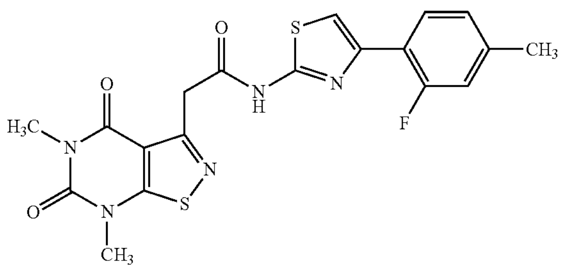 | 2-(5,7-Dimethyl-4,6-dioxo-4,5,6,7-tetrahydro[1,2]thiazolo[5,4-d]pyrimidin-3-yl)-N-{4-[2-fluoro-4-methylphenyl]-1,3-thiazol-2-yl}acetamide | $C_{19}H_{16}FN_5O_3S_2$ | 445.50 |
| 3 | 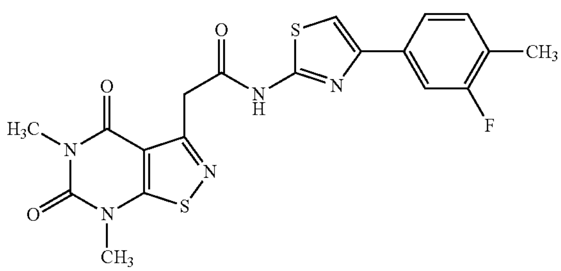 | 2-(5,7-Dimethyl-4,6-dioxo-4,5,6,7-tetrahydro[1,2]thiazolo[5,4-d]pyrimidin-3-yl)-N-{4-[3-fluoro-4-methylphenyl]-1,3-thiazol-2-yl}acetamide | $C_{19}H_{16}FN_5O_3S_2$ | 445.50 |
| 4 | 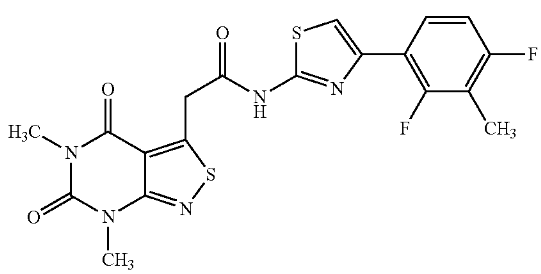 [SMILES: Cc1c(F)ccc(-c2csc(NC(=O)Cc3snc4c3c(=O)n(C)c(=O)n4C)n2)c1F] | N-{4-[2,4-Difluoro-3-methylphenyl]-1,3-thiazol-2-yl}-2-(5,7-dimethyl-4,6-dioxo-4,5,6,7-tetrahydro[1,2]thiazolo[3,4-d]pyrimidin-3-yl)acetamide | $C_{19}H_{15}F_2N_5O_3S2$ | 463.49 |
| 5 | 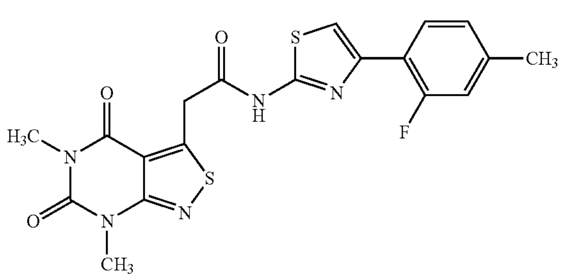 | N-{4-[2-fluoro-4-methylphenyl]-1,3-thiazol-2-yl}-2-(5,7-dimethyl-4,6-dioxo-4,5,6,7-tetrahydro[1,2]thiazolo[3,4-d]pyrimidin-3-yl)acetamide | $C_{19}H_{16}FN_5O_3S_2$ | 445.50 |

TABLE 3-continued

Additional examples of fluorinated furopyrimindiedione acetamide derivatives

| S No. | Molecular structure | Chemical name | Mol. Formula | Mol Wt. |
|---|---|---|---|---|
| 6 | [structure] | N-{4-[3-fluoro-4-methylphenyl]-1,3-thiazol-2-yl}-2-(5,7-dimethyl-4,6-dioxo-4,5,6,7-tetrahydro[1,2]thiazolo[3,4-d]pyrimidin-3-yl)acetamide | $C_{19}H_{16}FN_5O_3S_2$ | 445.50 |

Pharmacological Activity

The illustrative examples of the present invention are screened for TRPA1 activity according to a modified procedure described in (a) Tóth, A. et al. *Life Sciences*, 2003, 73, 487-498. (b) McNamara C, R. et al, *Proc. Natl. Acad. Sci. U.S.A.*, 2007, 104, 13525-13530. The screening of the compounds can be carried out by other methods and procedures known to persons skilled in the art.

Screening for TRPA1 Antagonist Using the $^{45}$Calcium Uptake Assay:

The inhibition of TRPA1 receptor activation was measured as inhibition of allyl isothiocyanate (AITC) induced cellular uptake of radioactive calcium.

Test compounds were dissolved in 100% DMSO to prepare 10 mM stock and then diluted using plain medium with 0.1% BSA and 1.8 mM $CaCl_2$ to get the desired concentration. The final concentration of DMSO in the reaction was 0.5% (v/v). Human TRPA1 expressing CHO cells were grown in F-12 DMEM medium with 10% FBS, 1% penicillin-streptomycin solution, and 400 µg/ml of G-418. Rat TRPA1 expressing CHO cells were grown in F-12 DMEM medium with 10% FBS, 1% penicillin-streptomycin solution, and 400 µg/ml of Zeocin. Cells were seeded 24 h prior to the assay in 96 well plates so as to get ~50,000 cells per well on the day of experiment. Cells were treated with the test compounds for 10 minutes followed by the addition of AITC at a final concentration of 30 µM (for human TRPA1) and/or 10 µM (for rat TRPA1) and 5 µCi/ml $^{45}Ca^{+2}$ for 3 minutes. Cells were washed and lysed using a buffer containing 1% Triton X-100, 0.1% deoxycholate and 0.1% SDS. Radioactivity in the lysate was measured in a Packard TopCount after addition of liquid scintillant. (Toth et al, *Life Sciences* (2003) 73, 487-498; McNamara C R et al, *Proceedings of the National Academy of Sciences*, (2007) 104, 13525-13530).

Concentration response curves were plotted as a % of maximal response obtained in the absence of test antagonist. $IC_{50}$ values can be calculated from concentration response curve by nonlinear regression analysis using GraphPad PRISM software.

The compounds prepared were tested using the above assay procedure and the results obtained are given in Table 4. Percentage inhibition at concentrations of 1.0 µM and 10.0 µM are given in the table along with $IC_{50}$ (nM) details for selected examples. The $IC_{50}$ (nM) values of the compounds are set forth in Table 4 wherein "A" refers to an $IC_{50}$ value of less than 50 nM, "B" refers to $IC_{50}$ value in range of 50.01 to 100.0 nM and "C" refers to an $IC_{50}$ values above 100.0 nM.

TABLE 4

In-vitro screening results of compounds of invention

| | human TRPA1 | | | rat TRPA1 | | |
|---|---|---|---|---|---|---|
| | Percentage inhibition | | $IC_{50}$ value | Percentage inhibition | | $IC_{50}$ value |
| Example | at 1.0 µM | at 10.0 µM | (nM) | at 1.0 µM | at 10.0 µM | (nM) |
| Example 1 | 95.23 | 100 | A | 71.29 | 100 | C |
| Example 2 | 99.71 | 100 | A | 34.88 | 43.78 | — |
| Example 3 | 95.54 | 99.5 | A | 68.51 | 98.26 | C |
| Example 4 | 99.76 | 99.99 | A | 72.22 | 100 | — |
| Example 5 | 98.12 | 99.13 | A | 95.6 | 98.5 | — |
| Example 6 | 99.29 | 99.64 | A | 97.34 | 99.34 | C |
| Example 7 | 100 | 99.48 | A | 79.39 | 100 | C |
| Example 9 | 98.4 | 98.06 | A | 94.74 | 94.14 | — |
| Example 10 | 99.92 | 100 | — | 35.23 | 68.40 | — |
| Example 11 | 100 | 100 | A | 22.87 | 39.67 | — |
| Example 12 | 98.4 | 99.18 | A | 94.58 | 99.49 | C |
| Example 13 | 99.65 | 99.8 | A | 99.32 | 99.32 | — |
| Example 19 | 99.73 | 100 | A | 99.49 | 99.27 | A |
| Example 20 | 99.64 | 99.77 | A | 99.65 | 100 | A |
| Example 21 | 99.47 | 99.99 | A | 100 | 100 | A |
| Example 22 | 100.00 | 100.00 | A | 98.34 | 100 | — |
| Example 23 | 99.32 | 100 | A | 100 | 100 | A |
| Example 24 | 99.56 | 100 | A | 100 | 99.77 | B |

TABLE 4-continued

In-vitro screening results of compounds of invention

| | human TRPA1 | | | rat TRPA1 | | |
|---|---|---|---|---|---|---|
| | Percentage inhibition | | $IC_{50}$ value | Percentage inhibition | | $IC_{50}$ value |
| Example | at 1.0 μM | at 10.0 μM | (nM) | at 1.0 μM | at 10.0 μM | (nM) |
| Example 25 | 99.89 | 100 | A | 98.78 | 100.00 | B |
| Example 26 | 99.9 | 99.5 | A | 97.74 | 100.00 | C |
| Example 27 | 97.83 | 99.83 | A | 81.78 | 99.60 | C |
| Example 28 | 98.02 | 99.6 | A | 92.85 | 100.00 | — |
| Example 29 | 98.07 | 99.63 | A | 100 | 100 | A |
| Example 30 | 95.59 | 99.71 | A | 100 | 99.31 | B |
| Example 31 | 99.15 | 99.20 | — | 99.59 | 96.16 | — |
| Example 32 | 99.20 | 99.40 | — | 99.81 | 100 | — |
| Example 37 | 98.33 | 99.33 | A | — | — | A |
| Example 38 | 100 | 99.87 | A | 100 | 100 | A |
| Example 39 | 99.76 | 99.87 | — | 96.54 | 95.79 | — |
| Example 40 | 99.81 | 99.91 | A | 98.96 | 99.19 | A |

The invention claimed is:

1. The compound having the structure (Id)

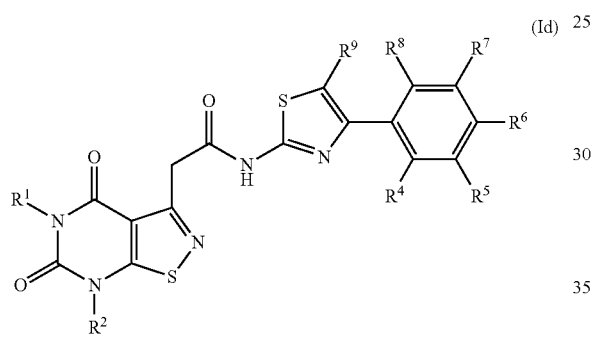

(Id)

or a pharmaceutically acceptable salt thereof;
wherein,
$R^1$ and $R^2$, which may be the same or different, are each independently hydrogen or $(C_1-C_4)$alkyl;
$R^4, R^5, R^6, R^7, R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

2. The compound according to claim 1, wherein $R^1$ and $R^2$ are $(C_1-C_4)$alkyl.

3. The compound according to claim 2, wherein $(C_1-C_4)$ alkyl is methyl.

4. The compound according to claim 1, wherein $R^4$ or $R^6$ is hydrogen, fluoro, chloro or bromo.

5. The compound according to claim 1, wherein $R^4$ or $R^6$ is methyl, ethyl, butyl, cyclohexyl, trifluoromethyl, difluoromethoxy or trifluoromethoxy.

6. The compound according to claim 1, wherein $R^5$ or $R^7$ is hydrogen, methyl, trifluoromethyl, difluoromethoxy or trifluoromethoxy.

7. The compound according to claim 1, wherein $R^5$ or $R^7$ is fluoro or chloro.

8. The compound according to claim 1, wherein $R^8$ or $R^9$ is hydrogen.

9. The compound according to claim 1 selected from:
N-[4-(4-Chlorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide;
2-(5,7-Dimethyl-4,6-dioxo-4,5,6,7-tetrahydro[1,2]thiazolo[5,4-d]pyrimidin-3-yl)-N-{4-[3-(trifluoromethyl)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[4-(trifluoromethoxy)phenyl]-1,3-thiazol-2-yl}acetamide;
N-[4-(4-Bromophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide;
2-(5,7-Dimethyl-4,6-dioxo-4,5,6,7-tetrahydro[1,2]thiazolo[5,4-d]pyrimidin-3-yl)-N-[4-(4-tert butylphenyl)-1,3-thiazol-2-yl]acetamide;
2-(5,7-Dimethyl-4,6-dioxo-4,5,6,7-tetrahydro[1,2]thiazolo[5,4-d]pyrimidin-3-yl)-N-[4-(4-ethyl phenyl)-1,3-thiazol-2-yl]acetamide;
2-(5,7-Dimethyl-4,6-dioxo-4,5,6,7-tetrahydro[1,2]thiazolo[5,4-d]pyrimidin-3-yl)-N-[4-(4-cyclohexylphenyl)-1,3-thiazol-2-yl]acetamide;
2-(5,7-Dimethyl-4,6-dioxo-4,5,6,7-tetrahydro[1,2]thiazolo[5,4-d]pyrimidin-3-yl)-N-{4-[3-fluoro-4-(trifluoromethyl)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[4-fluoro-3-(trifluoromethyl)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[2-fluoro-4-(trifluoromethyl)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[3-fluoro-5-(trifluoromethyl)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[2-fluoro-3-(trifluoromethyl)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[4-fluoro-3-(trifluoromethoxy)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[3-fluoro-4-(trifluoromethoxy)phenyl]-1,3-thiazol-2-yl}acetamide;
N-[4-(3,4-Dichlorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide;

N-[4-(3,4-Difluorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide;
N-[4-(2,4-Difluorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide;
2-(5,7-Dimethyl-4,6-dioxo-4,5,6,7-tetrahydro[1,2]thiazolo[5,4-d]pyrimidin-3-yl)-N-{4-[4-chloro-3-(trifluoromethyl)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[3-chloro-4-(trifluoromethoxy)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[4-chloro-3-(trifluoromethoxy)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[3-chloro-5-(trifluoromethyl)phenyl]-1,3-thiazol-2-yl}acetamide;
2-(5,7-Dimethyl-4,6-dioxo-4,5,6,7-tetrahydro[1,2]thiazolo[5,4-d]pyrimidin-3-yl)-N-{4-[2-fluoro-5-(trifluoromethyl)phenyl]-1,3-thiazol-2-yl}acetamide;
N-[4-(3,5-Dichlorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide;
N-{4-[4-(Difluoromethoxy)-3-fluorophenyl]-1,3-thiazol-2-yl}-2-(5,7-dimethyl-4,6-dioxo-4,5,6,7-tetrahydro[1,2]thiazolo[5,4-d]pyrimidin-3-yl)acetamide;
N-{4-[3-Chloro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide;
N-{4-[2,4-Difluoro-3-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide;
N-{4-[3,5-difluoro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide;
N-{4-[2,3-Difluoro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide;
N-{4-[4-(Difluoromethoxy)-3,5-difluorophenyl]-1,3-thiazol-2-yl}-2-(5,7-dimethyl-4,6-dioxo-4,5,6,7-tetrahydroisothiazolo[5,4-d]pyrimidin-3-yl)acetamide;
N-[4-(2,4-Dichloro-5-fluorophenyl)-1,3-thiazol-2-yl]-2-(5,7-dimethyl-4,6-dioxo-4,5,6,7-tetrahydro[1,2]thiazolo[5,4-d]pyrimidin-3-yl)acetamide;
and
or a pharmaceutically acceptable salt thereof.

10. The compound having the structure

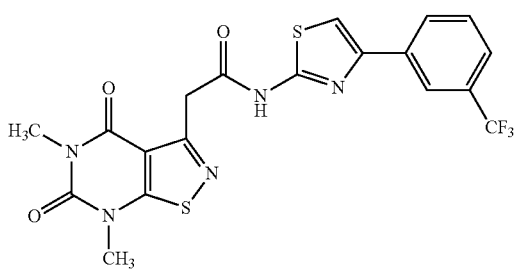 [SMILES: Cn1c(=O)c2c(CC(=O)Nc3nc(-c4cccc(C(F)(F)F)c4)cs3)nsc2n(C)c1=O]

or pharmaceutically acceptable salt thereof.

11. The compound having the structure

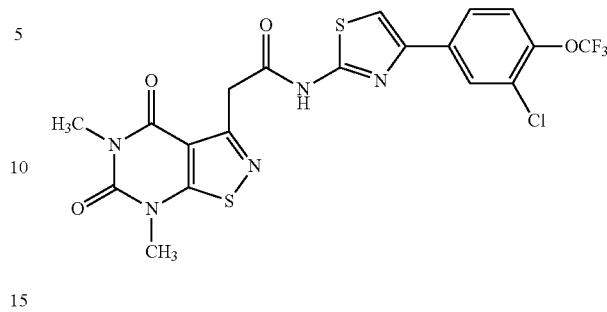

or pharmaceutically acceptable salt thereof.

12. The compound having the structure

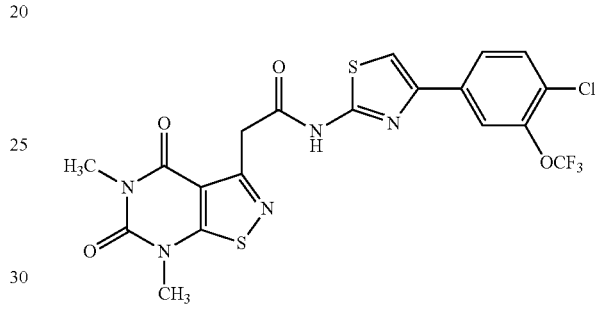

or pharmaceutically acceptable salt thereof.

13. The compound having the structure

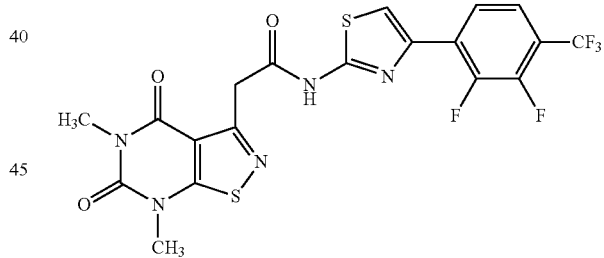

or pharmaceutically acceptable salt thereof.

14. A pharmaceutical composition comprising one or more compound according to claim 1, and one or more pharmaceutically acceptable excipients, carriers, diluents or mixture thereof.

15. A pharmaceutical composition comprising the compound of claim 13, and one or more pharmaceutically acceptable excipients, carriers, diluents or mixture thereof.

* * * * *